US010073025B2

(12) United States Patent
Bartels et al.

(10) Patent No.: US 10,073,025 B2
(45) Date of Patent: Sep. 11, 2018

(54) METHOD AND DEVICE FOR INCOHERENT IMAGING WITH COHERENT DIFFRACTIVE RECONSTRUCTION

(71) Applicant: Colorado State University Research Foundation, Fort Collins, CO (US)

(72) Inventors: Randy Bartels, Fort Collins, CO (US); Jeffrey J. Field, Fort Collins, CO (US); David G. Winters, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 15/268,308

(22) PCT Filed: Mar. 24, 2015

(86) PCT No.: PCT/US2015/022319
§ 371 (c)(1),
(2) Date: Sep. 16, 2016

(87) PCT Pub. No.: WO2015/148560
PCT Pub. Date: Oct. 1, 2015

(65) Prior Publication Data
US 2017/0184483 A1    Jun. 29, 2017

Related U.S. Application Data

(60) Provisional application No. 61/969,675, filed on Mar. 14, 2014.

(51) Int. Cl.
*G01N 15/00* (2006.01)
*G01N 15/14* (2006.01)
(52) U.S. Cl.
CPC ..... *G01N 15/1434* (2013.01); *G01N 15/1468* (2013.01)

(58) Field of Classification Search
CPC ........... G01N 21/6458; G01N 15/1434; G01N 15/1468; G01N 21/4795; G01N 27/228;
(Continued)

(56) References Cited

U.S. PATENT DOCUMENTS 5,956,355 A * 9/1999 Swanson ............ A61B 1/00183
356/479
2002/0105655 A1   8/2002 Svetkoff et al.
(Continued)

FOREIGN PATENT DOCUMENTS

WO   2010105015 A2   9/2010
WO   2014007763 A1   1/2014

OTHER PUBLICATIONS

Internation Search Report and Written Opinion, PCT/US15/22319, dated Mar. 24, 2015.

*Primary Examiner* — Michael P Stafira
(74) *Attorney, Agent, or Firm* — Maschoff Brennan; Paul G. Johnson

(57) ABSTRACT

Systems and methods are disclosed to determine the axial and/or lateral location of a particle using light modulated with temporal and/or spatial modulation pattern. The system, for example, may include a modulator configured to temporally modulate an intensity pattern of a line of light uniquely at each point along a lateral length of the line of light and produce an undiffracted modulated line of light, a first first-order diffracted line of light, and a second first-order diffracted line of light; and one or more optical elements configured to direct the undiffracted line of light and one of the first first-order diffracted line of light and the second first-order diffracted line of light toward at least one particle disposed at or near a sample region. The system may include a processor configured to determine an axial and/or a lateral position of the particle disposed at or near the sample region.

20 Claims, 12 Drawing Sheets

(58) Field of Classification Search
CPC ............ G02B 21/0024; G02B 21/0036; G02B 27/4244; G02B 5/1828; G02B 26/001; G02B 5/32; G02B 6/29395; G01B 11/0641; G01B 11/002
See application file for complete search history.

(56) References Cited

U.S. PATENT DOCUMENTS

| | | |
|---|---|---|
| 2007/0201123 A1 | 8/2007 | Saggau et al. |
| 2008/0049288 A1 | 2/2008 | Yun |
| 2008/0137697 A1 | 6/2008 | Maeda et al. |
| 2010/0284022 A1* | 11/2010 | Hsu .................. G01B 11/002 356/499 |
| 2011/0090511 A1 | 4/2011 | Medicus et al. |
| 2011/0223587 A1 | 9/2011 | Schulman et al. |
| 2014/0055594 A1 | 2/2014 | Nomura et al. |

* cited by examiner

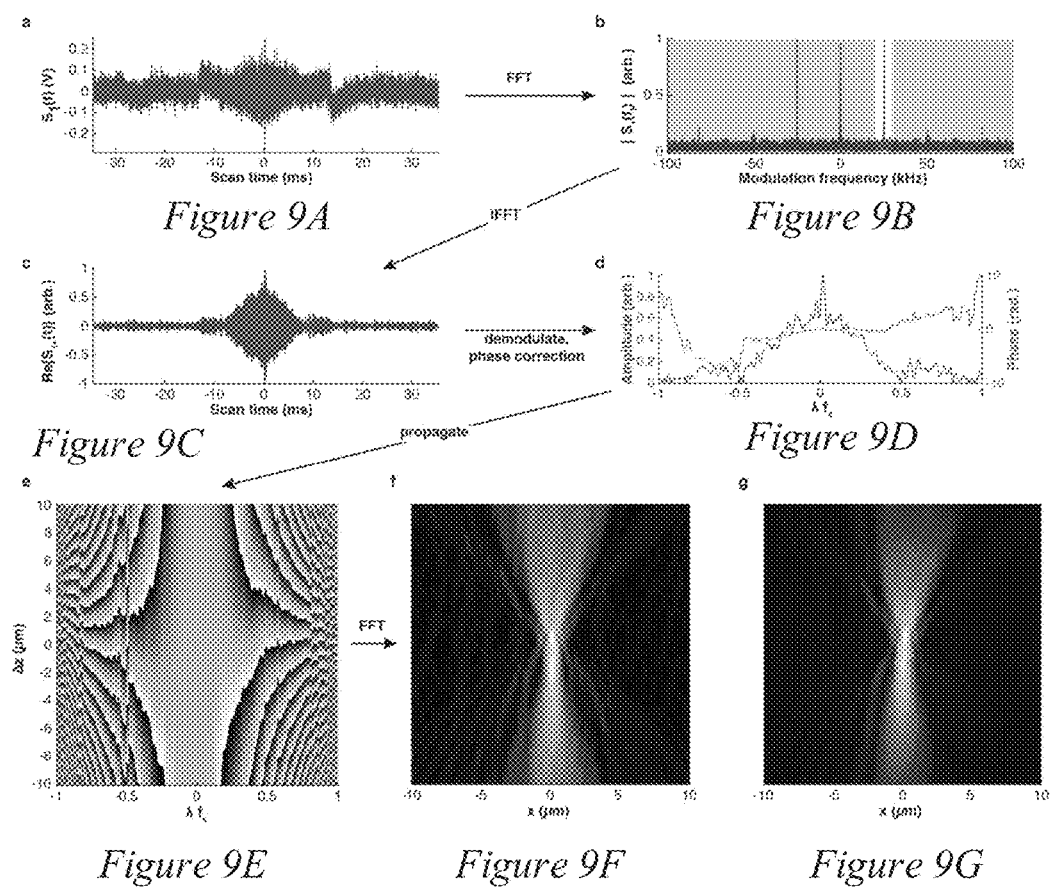
*Figure 9A*  *Figure 9B*  *Figure 9C*  *Figure 9D*  *Figure 9E*  *Figure 9F*  *Figure 9G*

METHOD AND DEVICE FOR INCOHERENT IMAGING WITH COHERENT DIFFRACTIVE RECONSTRUCTION

CROSS-REFERENCE TO RELATED APPLICATIONS

This application claims priority to PCT Application No. PCT/US2015/022319, filed Mar. 24, 2015, titled METHOD AND DEVICE FOR INCOHERENT IMAGING WITH COHERENT DIFFRACTIVE RECONSTRUCTION, which claims priority to U.S. Provisional Application No. 61/969,675, filed Mar. 24, 2014, titled METHOD AND DEVICE FOR INCOHERENT IMAGING WITH COHERENT DIFFRACTIVE RECONSTRUCTION.

BACKGROUND

The ability to spatially resolve the structure of objects may be helpful in understanding a number of physical systems and may provide insights into fields as diverse as astrophysics, molecular solvation dynamics, geophysical systems, the behavior of solid state materials, and biological systems. Likewise, temporal dynamics may be required for unraveling processes of physical systems in relation to internal and external stimuli. The capture of dynamic volumetric images from biological specimens may help unravel mysteries in diverse areas such as, for example, developmental biology, tumor growth, and tissue engineering.

Many biological processes are mediated chemically, and relevant mechanisms are often elucidated only by labeling these processes with fluorescent probes. Fluorescent imaging is pervasive in biological sciences owing to its molecular specificity, which allows for labeling of targeted processes. Current imaging techniques are limited in the speeds at which they can acquire 3D images of incoherent light (e.g., fluorescence). High speed 3D imaging of fluorescent light emission would be of great value in understanding biological dynamics by virtue of the ability to precisely label bio-chemicals of interest.

3D images formed from collection of incoherent light can be obtained with high spatial resolution using techniques that restrict illumination and/or detection to a small volume in the sample region. For example, high fidelity imaging of 3D fluorophore distributions is permitted by confocal and two-photon laser scanning microscopy (LSM). However, restricting data collection to a small volume may require serial data acquisition, which might limit imaging speed and/or may degrade the ability to track dynamic behavior in 3D. Although various techniques have been reported for improving the speed of data acquisition in LSM by multi-focal techniques, parallelization of data acquisition is limited to the number of foci, imposing practical limitations on the update rate of such systems.

Conversely, illumination with a coherent radiation beam may allow for the possibility of exploiting diffraction to image the spatial organization of a specimen in a single shot, drastically increasing imaging speeds. Since the only requirements for obtaining such an image are recovery of the amplitude and phase of the diffracted coherent field, and adherence to the first Born or Rytov approximations, diffractive volumetric imaging can, in principle, span the electromagnetic spectrum. Volumetric imaging exploiting the physics of coherent wave diffraction, i.e., encoding propagation distance in the diffracted beam phase, has proven useful in seismic, ultrasonic and photo acoustic, optical, x-ray, and electron beam imaging systems for rapid detection of spatial organization and temporal dynamics.

These techniques, generally referred to as coherent diffractive imaging (CDI), rely on the recording, or numerical recovery, of optical phase information that reveals the distance the light has travelled from the point at which it scatters in an object to where it is recorded with a detector. Reconstruction of a volumetric image is based on a model of propagation, possibly combined with a priori knowledge about the specimen.

Spatial phase information may not be directly detectable at optical frequencies, so interferometric techniques are conventionally used to extract the phase and amplitude of the diffracted signal field. Off axis holography is the most successful of these methods. In off axis holography a coherent reference beam bypasses the specimen and is made to interfere with light coherently scattered by the specimen from the illumination beam. In the lateral and axial dimensions, the coherent scattered beam accumulates a spatial phase of the form $e^{[i\pi(\lambda \Delta z)^{-1}(x-\Delta x)^2]}$ far from a scattering point, where $\Delta z$ is the (axial) propagation distance and $\Delta x$ is the lateral location. The resulting interference pattern is recorded with a detector array, e.g., a camera, and contains intensity modulations proportional to $\cos[1+\pi(\lambda \Delta z)^{-1}(x-\Delta x)^2]$ that encode the phase difference between the two beams, $\phi=1+\pi(\lambda \Delta z)^{-1}(x-\Delta x)^2$. Phase information represents the location of coherent scattering locations in the object that are encoded as intensity modulations in the recorded image. With these methods, spatial phase recovery is only possible if coherence is maintained between object and reference optical fields. In digital holographic microscopy (DHM), the complex field (magnitude and phase) of the beam diffracted from the object is recovered and numerically refocused to the sample region, producing a volumetric representation of the object.

Alternatively, the amplitude and phase of a coherent field diffracted from an object can be recovered through inversion of coherent light propagation with a regularized, iterative optimization algorithm, negating the need to form an interference pattern. This type of imaging is often called lensless CDI, and a wide range of related techniques fall under this umbrella. These techniques have found widespread application in high-resolution imaging of nano scale objects, including biological specimens such as yeast and chromosomes. Until now the power of DHM and CDI has been largely inaccessible to fluorescent light emission due to the random phase of the emitted fluorescent light, which renders it incoherent. The lack of a deterministic phase relationship between emitters in the object rules out image reconstruction by spatial phase inversion. Because of the vast potential of increasing imaging speed, adaptation of coherent imaging techniques to incoherent light is a long-sought, yet elusive, goal in optical imaging. For example, methods for obtaining holograms with incoherent light have been studied since the early days of holography. Generally, these efforts attempted to project illumination structured with Fresnel zone plate (FZP) rings, or similar patterns, into a sample and then record the transmitted light. The spacing of the oscillations in the measured FZP rings is related to the propagation distance, thereby encoding depth information into the interference pattern. Adaptation of this method for fluorescently emitting objects has been implemented in optical scanning holography and fluorescence incoherent correlation holography.

SUMMARY

Systems and methods are disclosed to determine the axial and/or lateral location of a particle using light modulated with temporal and/or spatial modulation pattern. The system, for example, may include a modulator configured to temporally modulate an intensity pattern of a line of light uniquely at each point along a lateral length of the line of light and produce an undiffracted line of light (e.g. undiffracted modulated line of light), a first first-order diffracted line of light, and a second first-order diffracted line of light; and one or more optical elements configured to direct the undiffracted line of light and one of the first first-order diffracted line of light and the second first-order diffracted line of light toward at least one particle disposed at or near a sample region. The system may include a processor configured to determine an axial and/or a lateral position of the particle disposed at or near the sample region.

In some embodiments, the system may include one or more optical elements that produce the line of light from a light source. In some embodiments, the one or more optical elements may include a spatial filter having at least a single slit and/or a cylindrical lens.

In some embodiments, the modulator may include at least one of a patterned mask, an acousto-optical modulator, an acousto-optical deflector, and/or a circular modulation mask. In some embodiments, the one or more optical elements may direct the unmodulated line of light and one of the first first-order line of light and the second first-order line of light to interfere at or near the sample region.

In some embodiments, the light source may produce coherent light and the system may include a detector that detects incoherent light.

A system is also disclosed that includes a light source, a modulator, one or more optical elements, a detector, and/or a processor. In some embodiments, the light source may produce a beam of light and the modulator may be disposed in an optical path of the beam of light and may temporally modulate an intensity pattern of the beam of light uniquely at each point along a focus of the beam of light. The one or more optical elements may be configured to direct light from the modulator toward a sample region. The detector may be configured to detect light from the sample region. The processor may be electrically coupled with the detector and configured to determine an axial position of a particle disposed at or near the sample region based on the intensity pattern of light detected at the detector.

In some embodiments, the modulator may produce two first-order diffracted beams of light and an undiffracted beam of light.

In some embodiments, the modulator may produce two first-order diffracted beams of light and an undiffracted beam of light. The system may also include an optical element configured to direct at least one of the two diffracted beams of light and the undiffracted beam of light to interfere at the sample region.

In some embodiments, the modulator may produce two first-order diffracted beam of light and an undiffracted beam of light. The system may also include a filter that filters out all but one first-order diffracted beam of light.

In some embodiments, the modulator modulates a frequency imparted to a line focus that varies linearly with a function of lateral position.

In some embodiments, the modulator may include at least one of a patterned mask, an acousto-optical modulator, an acousto-optical deflector, and/or a circular modulation mask. A method may also include producing a line of light with a light source; modulating the line of light both temporally and spatially along a lateral length of the line of light into modulated light; directing the modulated light toward a sample region; detecting, with a light detector, light from at least one particle disposed at or near the sample region; and determining an axial position of the particle from an intensity pattern of the detected light. In some embodiments, the light source may include an optical element comprising either or both a cylindrical lens and an optical element with a slit.

In some embodiments, the line of light may be modulated with at least one of the following devices a patterned mask, an acousto-optical modulator, an acousto-optical deflector, and/or a circular modulation mask.

In some embodiments, the modulated light may include at least two diffracted beams of light. In some embodiments, the method may include filtering out at least one of the at least two diffracted beams of light.

In some embodiments, the modulated light may include an undiffracted beam of light and a diffracted beam of light. The method may further include directing the undiffracted beam of light and the one diffracted beam of light to interfere at or near the sample region.

In some embodiments, the method may include determining a lateral position of the particle from an intensity pattern of the detected light.

In some embodiments, the method may include generating a signal proportional to the intensity of the light from a particle disposed at or near the sample region, and wherein the determining an axial position of the particle comprises solving a function of a frequency of the signal.

In some embodiments, an axial position of the particle may be determined from an intensity pattern of the detected light includes calculating a Fourier transform of the intensity pattern of the detected light.

BRIEF DESCRIPTION OF THE FIGURES

FIGS. 9A-9G illustrate a method for determining a lateral or axial position of a particle from a detector signal according to some embodiments.

DETAILED DESCRIPTION

Figure 1:
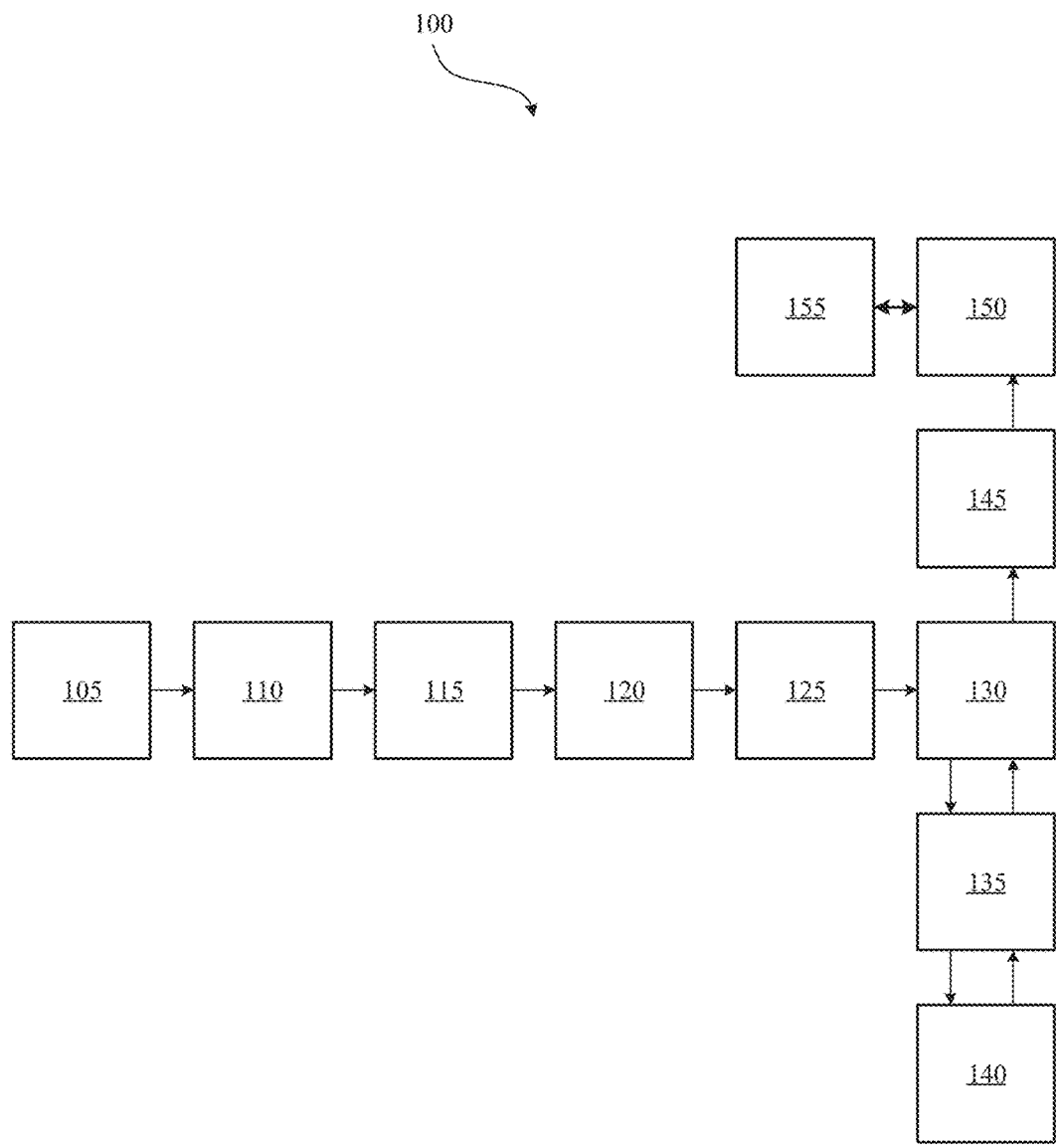
FIG. 1 illustrates a block diagram of an imaging system according to some embodiments described within this document.

Some embodiments of the invention include an imaging method and/or system that use modulated light to determine the location (e.g., the axial and/or the lateral location) of one or more particles in a sample region. The modulated light, for example, may be modulated with a spatial and/or temporal modulation pattern. The modulated light, for example, may include one or more light beams that combine to produce a unique temporal illumination intensity patterns for each position in the sample region. As another example, the modulated light may be coherent and the propagation phase of the modulated light may be transferred to incoherent light after interaction (e.g., fluorescence, emission, scatter, refraction, reflection, etc.) with a particle disposed in a sample region. The axial location of the particle, for example, may be determined based on a temporal intensity pattern of light detected from the particle, which varies as a function of time.

In some embodiments, a contrast mechanism may be used to detect absorption of the illumination beam (either transmitted or back-scattered) such as, for example, electronic absorption (e.g., oxygenated and deoxygenated hemoglobin), molecular overtone absorption (e.g., CH3 groups in type I collagen, CH2 bonds in lipids), phosphorescence, and Förster resonance energy transfer (FRET). The particles in the sample region, for example, may include a contrast mechanism that depends on the illumination intensity such as, for example, Raman and fluorescence.

Various types of detection geometry may be used such as, for example, epi-fluorescent, transmitted, scattered, and reflective, etc. In some embodiments, the scattering or emission from multiple directions may be summed to form a composite image, which may be helpful, for example, for weakly scattering or weakly emitting specimens.

In some embodiments, the modulation light may include multiple illumination beams with temporal modulation patterns that combine to produce unique temporal illumination intensity patterns for each position in the sample region. For example, two illumination beams may be used to produce an illumination intensity pattern, I(x,y,z,t), with unique temporal modulation intensity at each point in the transverse-axial plane (e.g., the (x, z) plane). The two beams, for example, may include an undiffracted beam and a first-order diffraction beam.

In some embodiments, a configuration with multiple illumination beams may, for example, ensure that no two points in the transverse-axial plane will be subject to the same illumination intensity pattern.

In some embodiments, an initial coherent beam to a line of light may be focused on a modulator using any technique known in the art. The line of light, for example, may include a small distribution of the beam in the vertical direction. A horizontal slit, for example, may be used to produce the line of light. As another example, a cylindrical lens may be used to produce the line of light.

In some embodiments, the illumination intensity in the sample region may be calculated by a plane wave expansion of the diffracted orders from the modulator. The spatial phase difference, $\phi$, between the two illumination beams may be written:

$$\phi = 2\pi\Delta x\left(\frac{n_o}{n_m}M\kappa t\right) - kn_o z\left[\sqrt{1 - \left(\frac{\lambda M\kappa t}{n_m}\right)^2} - 1\right] + \phi_f,$$

where $\phi_f$ is a temporal phase shift acquired by the emitted fluorescence intensity, $m_f$ is the change in the emitted fluorescence intensity modulation depth, x is the lateral location relative to the centroid of the illumination intensity distribution, $\kappa$ is a parameter introduced by the modulation mask and may include the linear change in temporal modulation frequency as a function of lateral coordinate, M is the demagnification of the imaging optics, $\lambda$ is the wavelength of the illumination light, and $\Delta z$ is the axial location relative to the focal plane of the imaging system.

In some embodiments, the time-dependent illumination intensity in the sample region varies as:

$$I(x, z, t) \propto m_f \cos(\phi) \propto$$
$$m_f \cos\left[2\pi\Delta x\left(\frac{n_o}{n_m}M\kappa t\right) - kn_o z\left[\sqrt{1 - \left(\frac{\lambda M\kappa t}{n_m}\right)^2} - 1\right] + \phi_f\right].$$

The spatial phase difference, $\phi$, between the two illumination beams may be written for the paraxial approximation as:

$$\phi = m_f \cos\left[2\pi\Delta x(M\kappa t) - \pi\lambda\Delta z(M\kappa t)^2\right].$$

In some embodiments, the time-dependent illumination intensity in the sample region varies as:

$$I(x,z,t) \propto m_f \cos\left[2\pi\Delta x(M\kappa t) - \pi\lambda\Delta z(M\kappa t)^2\right]$$

where In some embodiments, this equation may be used to determine a lateral and/or axial (x, z) position in the sample region and may be associated with a unique temporal illumination intensity modulation that varies with scan time and position.

Some embodiments use two (or more) beams with a spatially dependent temporal frequency to interfere in the sample region to produce an interference pattern with unique temporal frequency in the lateral and axial directions. The two (or more) beams with a spatially dependent temporal frequency may interfere in the sample region to produce an interference pattern with unique temporal frequency in three dimensions horizontal (lateral), vertical (lateral), and axial directions.

Some embodiments of the invention position a horizontal line filter (for filtering one of the two diffracted beams) near a back focal plane of the imaging objective of the microscope system; modulation plane and/or the sample region to be conjugate image planes. In some embodiments, the spatial filter may be placed away from the modulation plane and/or the sample region.

In some embodiments, the modulation plane and/or the sample region may be image conjugates. For example, the imaging system may include a pair of lenses with multiple image relay optics between the modulator and the object.

In some embodiments, a multiple detector systems may be used and the signal from the multiple detectors may be summed.

In some embodiments, a line array CCD may be used to achieve hyperspectral detection. In some embodiments, a spectrometer may be placed where the photodetector is typically placed. Each pixel of the linear CCD array may, for example, act like a single element detector reporting spatial information for a single wavelength.

FIG. 1 illustrates an imaging system 100 includes a light source 105, one or more optical elements 110, a modulator 115, an optical element 120, a filter 125, a beam splitter 130, one or more optical elements 135, a sample region 140, one or more optical elements 145, a detector 150, and a processing unit 155. In some embodiments, various other components may be used. Moreover, the various components shown in FIG. 1 may be rearranged in other configurations. In some embodiments, one or more components may be eliminated. In some embodiments, the light source 105 may include any light source that produces coherent light. In some embodiments, the light source may include a laser such as, for example, a continuous wave laser, a pulsed laser, a chirped laser, etc. In some embodiments, the light source may produce light having a wavelength that is tuned to the wavelength that may be used to fluoresce a sample. In some embodiments, the fluorescing material may be selected based on the light source 105. In some embodiments, the light source may produce coherent light. In some embodiments, the light source may produce a collimated, spatially-coherent beam of light that is directed toward the one or more optical elements 110.

In some embodiments, the one or more optical elements 110 may include one or more passive optical elements such as, for example, one or more lenses. In some embodiments, the one or more optical elements 110 may include a cylindrical lens. In some embodiments, the one or more optical elements 110 may include an optical element that produces a light sheet. In some embodiments, the one or more optical elements 110 may focus a line of light from the light source on the modulator 115. In some embodiments, the one or more optical elements 110 may include an optical element(s) that focuses light from the light source in only one direction.

In some embodiments, the one or more optical elements 110 may include an objective lens that may spatially filter the beam of light. In some embodiments, the one or more optical elements 110 may include a pinhole. In some embodiments, the objective lens and/or the pinhole may be used to produce a nearly diffraction-limited beam of light. In some embodiments, the one or more optical elements 110 may include an achromatic lens that may collimate the diffraction limited beam of light. In some embodiments, the achromatic lens may produce a beam of light with any type of an intensity profile such as, for example, a Gaussian intensity profile.

In some embodiments, the modulator 115 may include any device that produces temporally modulated intensity pattern that is unique at each point along the focus. In some embodiments, the modulator may modulate the incident light temporally and spatially. In some embodiments, the modulator 115 may modulate the frequency imparted to a line focus that varies linearly with a function of lateral position, x. In some embodiments, the modulator 115 may modulate the frequency imparted to a line focus that varies linearly with a function of vertical position, y. In some embodiments, the modulator 115 may modulate the frequency imparted to a focus that varies in two dimensions as a function of position in two-dimensions, (x, z).

In some embodiments, a mask pattern may produce two diffracted light beams in the vertical (y) dimension to allow for the selection of one of the first-order diffracted light beams. The separation of the two first-order diffracted light beams may depend on the density of the modulation mask, $\Delta k$; the wavelength of the illumination light; and the optical system.

In some embodiments, the modulator 115 may include a patterned mask, an acousto-optical modulator, an acousto-optical deflector, or a circular modulation mask.

Figure 3:
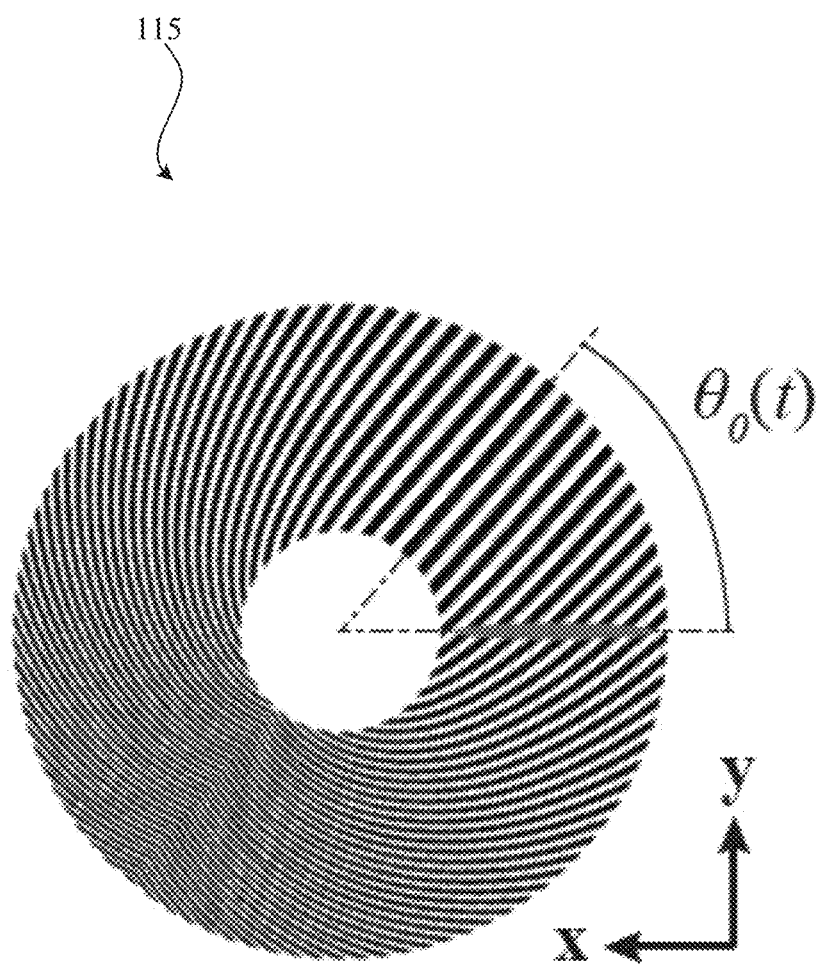
FIG. 3 illustrates an example of a circular modulation mask according to some embodiments described within this document.

In some embodiments, the modulator 115 may include a circular modulation mask as shown in FIG. 3. In some embodiments, a pattern such as, for example, the pattern shown in FIG. 3 may be printed onto a substrate such as, for example, aluminum printed onto a glass substrate. In this example the circular modulation mask is defined by $\Delta k=3/$mm. The circular modulation mask may be defined by various other $\Delta k$ values. In some embodiments, the circular modulation mask may be rotated with a constant velocity using, for example, a motor. As the mask is spun at a constant angular velocity, the modulation frequency varies linearly as a function of radius. The resultant modulation may be a function of the angle of rotation, $\theta_0$, which may be set based on user input. Because the circular modulation mask rotates at a constant velocity, $\theta_0=2\pi f_r$, where $f_r$ is the angular frequency of the mask. In some embodiments, the pattern produced by the circular modulation mask as it is rotating may be written as:

$$m(R,\theta)=\tfrac{1}{2}+\tfrac{1}{2}\,\mathrm{sgn}[\cos(\Delta kR\theta)],$$

where $\Delta k$ is the highest density of the modulation pattern. In Cartesian coordinates the pattern may be written as:

$$m(x, y, t) = \frac{1}{2} + \frac{1}{2N}\sum_{p=1}^{N} \cos(2\pi\kappa p t x + \Delta k y),$$

wherein N is the number of diffracted waves. If only the undiffracted beam is used with one of the first order diffracted beams, this pattern can be written as:

$$(x,y,t)=\tfrac{1}{2}+\tfrac{1}{2}\cos(2\pi\kappa tx+\Delta ky).$$

Figure 2:
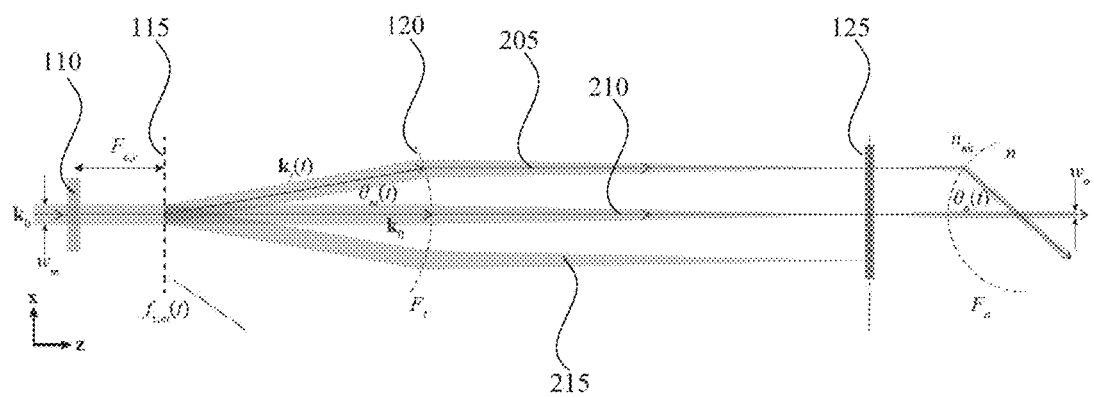
FIG. 2 illustrates three beams of light being directed from a modulator toward a filter according to some embodiments described within this document.

In some embodiments, the modulator 115 may produce two or more beams of light, such as, for example, two or more sheets of light or two or more lines of light. As shown in FIG. 2, the modulator 115 may produce an undiffracted beam of light 210, a first first-order diffracted beam of light 205, and a second first-order diffracted beam of light 215. In some embodiments, an intensity modulation pattern that is unique for every point in the lateral-axial pane (e.g., the x-z plane or the y-z plane) may be formed at the sample region via interference of the two light sheets of light.

In some embodiments, the intensity modulation pattern may extend through the lateral-axial plane at or near the sample region and over the scan time. Thus, in some embodiments, the interference between light beams may create a unique intensity modulation pattern that allows for identification of each spatial location at or near the sample region. A transverse spatial position, for example, may be tagged by the modulation frequency that is imparted by the modulation mask design. An axial position, for example, may be imparted through the temporal phase shift.

In some embodiments, the optical element 120 may be used to focus light from the modulator 115 toward the filter 125. In some embodiments, the optical element 120 may be a focal element or a focal system. In some embodiments, the optical element 120 may focus each of the two or more beams of light from the modulator toward the filter 125.

In some embodiments, the filter 125 may include one or more slits that block one or more diffracted beams of light. In some embodiments, the filter 125 may include a spatial filter that is disposed in the Fourier plane of the modulator 115 or the pupil plane of the optical element 120. In some embodiments, the filter 125 may allow an undiffracted light beam and a single diffracted order light beam to pass through the filter 125. In some embodiments, the filter 125 may remove the ambiguity of sign in the accumulated spatial phase. In some embodiments, the filter 125 may allow unique measurement of the spatial phase difference between an undiffracted illumination beam and a diffracted illumination beam.

FIG. 2 illustrates three beams of light beams directed from the modulator 115 toward the filter 125. These three beams of light include a first first-order diffracted beam of light 205, an undiffracted beam of light 210, and a second first order diffracted beam of light 215. The modulator 115 may produce other beams of light. The optical element 120 directs the light toward the filter 125. The filter 125 blocks the second first-order diffracted beam of light 215 and allows the undiffracted beam of light 210 and the first first-order diffracted beam of light 205 to pass through.

Figure 4:
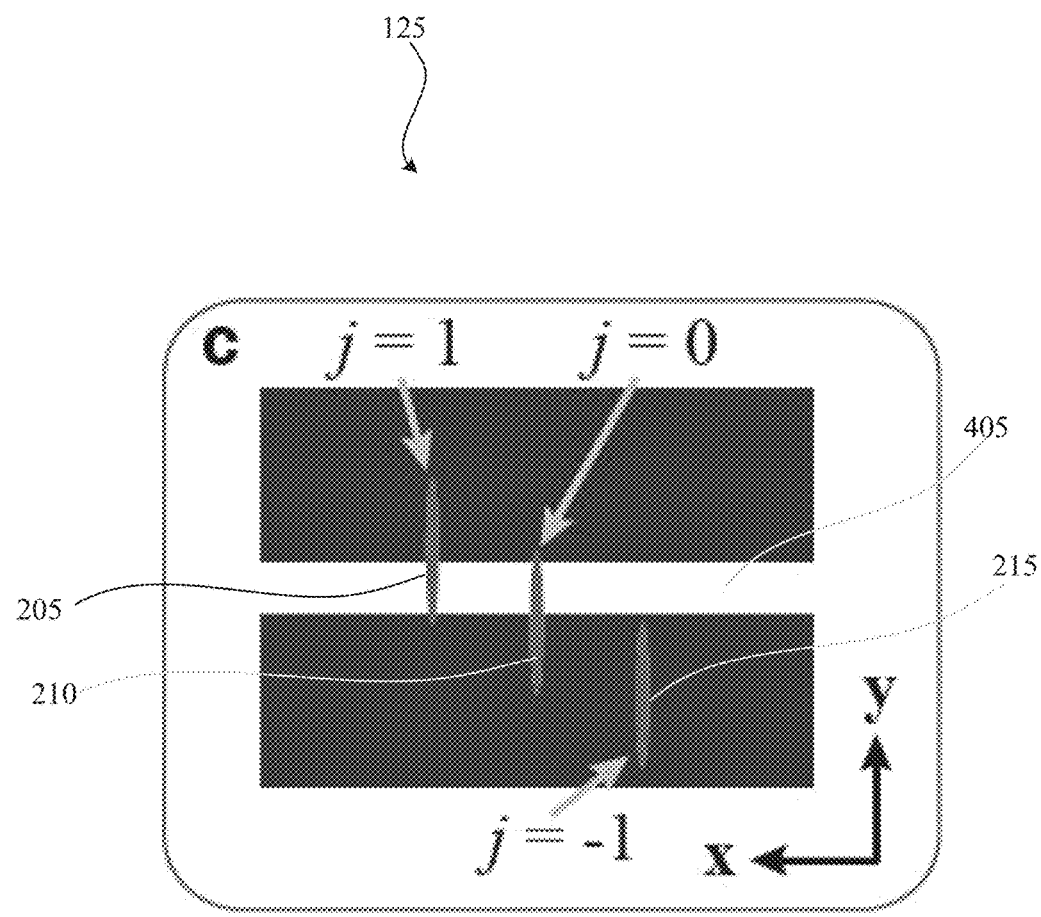
FIG. 4 illustrates an example filter according to some embodiments described within this document.

FIG. 4 illustrates a filter 125 with a slit 405. In this example the slit 405 filters out all light except for an undiffracted beam of light and one first-order diffracted beam of light. Various other slits or the like may be used to filter out one or more beams of light.

In some embodiments, the beam splitter 130 may include any device that may direct light from the modulator 115 toward the sample region 140 and allow light from the sample region 140 to pass through to the detector 150. In some embodiments, the beam splitter may include a dichroic mirror.

In some embodiments, the one or more optical elements 135 may include one or more passive optical elements such as, for example, one or more lenses. In some embodiments, the one or more optical elements 135 may include a cylindrical lens. In some embodiments, the one or more optical elements 135 may include an optical element that produces a light sheet. In some embodiments, the one or more optical elements 135 may focus a line of light from the light source on the sample region 140. In some embodiments, the one or more optical elements 135 may include an optical element(s) that focuses light from the beam splitter 130 toward the sample region 140.

In some embodiments the sample region 140 may include a particle, molecule, cell, an object, etc. In some embodiments, the sample may include one or more fluorophores or fluorescent beads. In some embodiments, the sample region 140 may include any contrast mechanism or media that produces light as a function of the illumination intensity such as, for example, Raman and fluorescence. In some embodiments, the sample may include oxygenated and deoxygenated hemoglobin. In some embodiments, the sample may include a contrast mechanism such as, for example, electronic absorption, molecular overtone absorption (e.g., CH3 groups in type I collagen, CH2 bonds in lipids, etc., phosphorescence, FRET, etc.

In some embodiments, coherent light or incoherent light incident on one or more fluorescent particles in the sample region 140 may be converted to incoherent light emitted by the fluorescent particles.

In some embodiments, a contrast mechanism may be used in conjunction with one or more particles disposed or placed in the sample region 140. The contrast mechanism, which can be coherent or incoherent, responds to this modulation pattern and re-emits, transmits, or scatters signal light that has the same spatio-temporal structure as the illumination intensity. In some embodiments, the one or more optical elements 145 may include one or more passive optical elements such as, for example, one or more lenses. In some embodiments, the one or more optical elements 145 may include a cylindrical lens. In some embodiments, the one or more optical elements 145 may include an optical element that produces a light sheet. In some embodiments, the one or more optical elements 145 may focus a line of light from the light source on the detector 150. In some embodiments, the one or more optical elements 145 may include an optical element(s) that focuses light from the sample region 140 and focuses the light on the detector 150.

In some embodiments, the one or more optical elements 145 may reimage, magnify, and/or demagnify light from the sample region 140. In some embodiments, the one or more optical elements 145 may include, for example, an achromatic lens, a tube lens and/or an objective lens.

In some embodiments the detector 150 may be a single-element photodetector such as, for example, a photomultiplier tube. In some embodiments, spatio-temporally modulated signal light from one or more particles in the sample region may be received by the detector 150. In some embodiments, the detector 150 may provide a periodic voltage signal, S(t). In some embodiments, the detector 150 may include a segmented detector such as, for example, a charge-coupled device (CCD), an active pixel device, a complementary metal-oxide-semiconductor (CMOS) device, etc. In some embodiments, the voltage from each pixel of a segmented detector may be summed. In some embodiments, the detector 150 may produce a voltage signal, S(t), that varies as the position of a particle in the sample region.

In some embodiments, the detector 150 may include a line-array detector (or CCD), which may allow hyperspectral detection. In some embodiments, a spectrometer may be disposed near the detector 150. Each pixel of the line-array detector may act like a single-element detector reporting spatial information for a given wavelength.

In some embodiments, the intensity pattern may vary as a function of four dimensions, I(x,y,z,t), or as a function of three dimensions I(x,z,t) or I(y,z,t). In some embodiments, the intensity pattern may be unique for each position in a given period of time. In some embodiments, the intensity pattern may encode the position of a particle based on the unique temporal modulations to the illumination intensity provided by the modulator 115. In some embodiments, the processing unit 155 may be communicatively coupled with the detector 150 and may receive electric signals from the detector 150 that are proportional to the intensity of the light incident on the pixels. For example, the data received by the processing unit 155 from the detector 150 may include an intensity pattern as a function of time and dimension. In some embodiments, the processing unit 155 may determine either or both the axial or lateral position of a particle in the sample region 140. In some embodiments, the processing unit 155 may include one or more digitizers, amplifiers, and/or one or more electronic filters.

In some embodiments, the processing unit 155 may receive a voltage signal, S(t), from the detector 150. Various techniques may be used to extract an axial or lateral position of a particle from the signal, S(t). For example, the processing unit 155 may calculate the Fourier transform of the signal, S(t), to create a reconstructed image of the particle at or near the sample plan.

Mathematically, this demodulation and propagation operation may be described as:

$$S_{1+}^{(r)}(x, z) = \hat{\mathcal{F}}_{f_x}\left\{S_{1+}(f_x)\exp\left[\mp i\frac{2\pi}{\lambda}n_o\Delta z\left\{\sqrt{1-\left(\frac{n_o}{n_m}\lambda f_x\right)^2}-1\right\}\right]\right\}$$

where the superscript (r) is used to denote the refocused data, $\mathcal{F}_{fx}$ is the Fourier transform operator with respect to lateral spatial frequency, $S_{1+}(f_x)$ denotes the complex data, which may be synthesized from the measured real-value data in the temporal domain, $\lambda$, denotes the wavelength of the light received from the sample, $S_1(t)$, by a Hilbert transform, $\Delta z$ is the defocus distance, and $f_x$ is the modulation frequency of the mask along the lateral direction.

$n_o$ denotes the refractive index of the sample region and $n_m$ denotes the refractive index of the medium within which the modulator is disposed. In some embodiments, it may be assumed that $n_o$ and $n_m$ are the same or that they are both in air. In such embodiments, therefore, the term $$\frac{n_0}{n_m}$$

may be included into the equations to represent this difference.

In some embodiments, the processing unit 155 may calibrate the system in various ways. For example, the lateral spatial axis may be calibrated using $$x = f_t / \left(\frac{n_o}{n_m}\kappa M\right) = f_t / \left(f_r \frac{n_o}{n_m}\Delta\kappa M\right),$$

where $f_t$ is the temporal modulation frequency, $f_r$ is the rotation frequency of the mask, $\Delta k$ is a known design parameter of the mask, and M is the magnification of the illumination microscope. In some embodiments, the rotation frequency, for example, may be determined empirically by digitizing the temporal signal over approximately 1.2 times the time period for one rotation $1/f_r$, and measuring the peak-to-peak time separation of the maximum signal from the modulation pattern that occurs near zero spatial frequency. Various other techniques may be used to determine the rotation frequency of the modulator.

Figure 12:
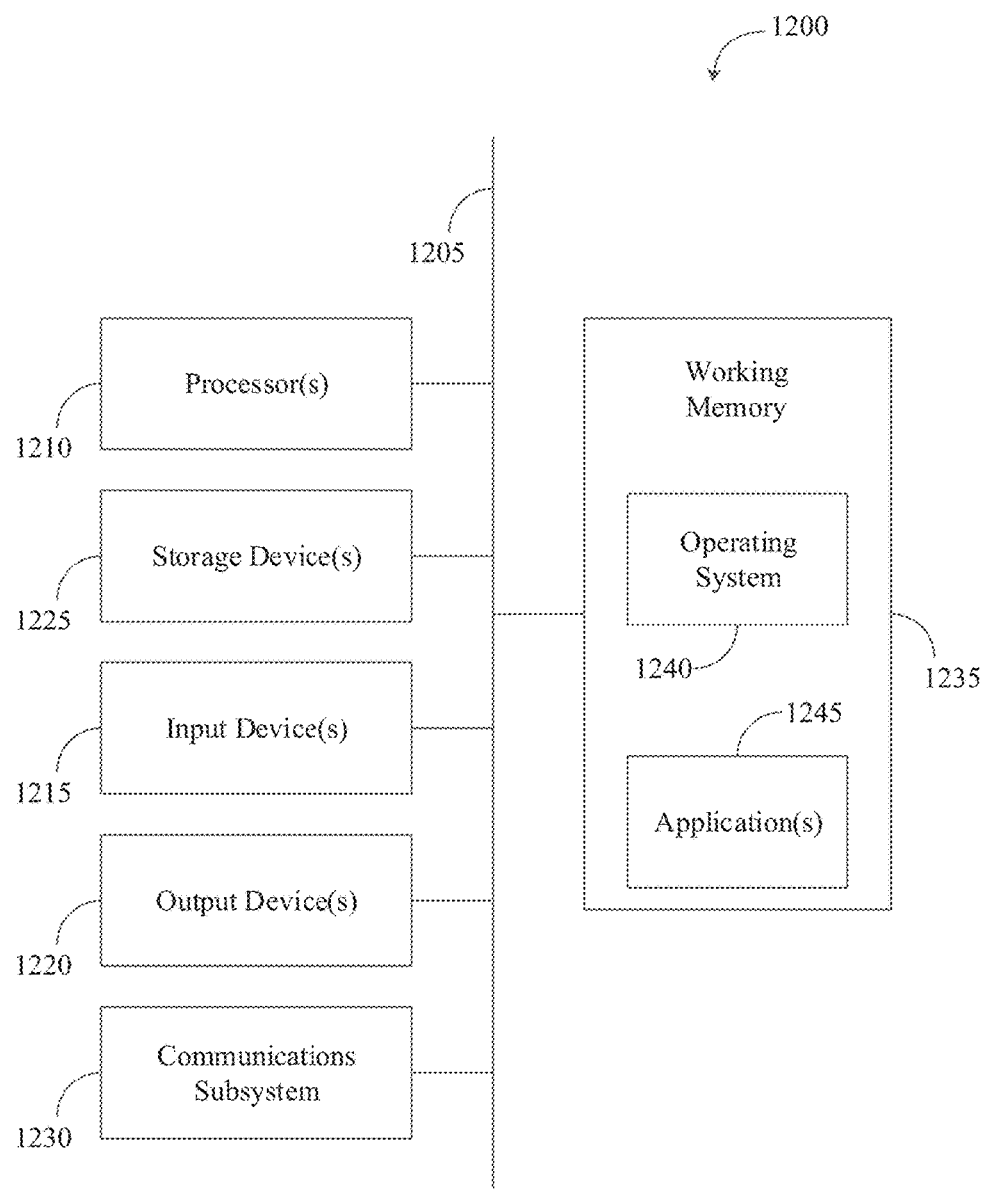
FIG. 12 shows an illustrative computational system for performing functionality to facilitate implementation of embodiments described herein.

In some embodiments, the processing unit 155 may include one or more components of the computational system 1200 shown in FIG. 12.

Figure 5:
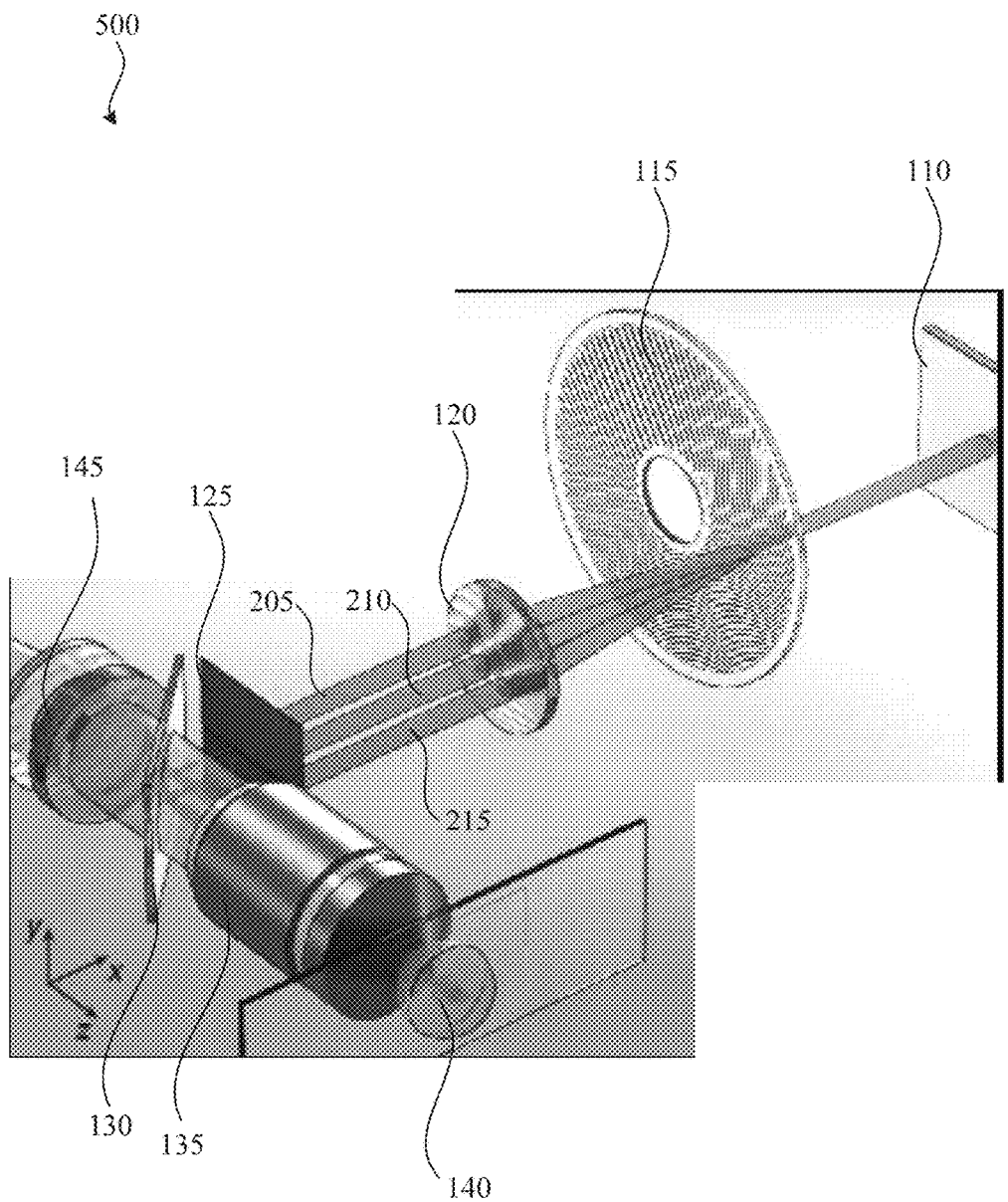
FIG. 5 illustrates an imaging system according to some embodiments described within this document.

FIG. 5 illustrates an imaging system 500 according to some embodiments described within this document. The imaging system 500 includes one or more optical elements 110, a modulator 115, an optical element 120, a filter 125, a beam splitter 130, one or more optical elements 135, a sample region 140, and one or more optical elements 145. A detector and a processing unit may also be included.

Figure 6:
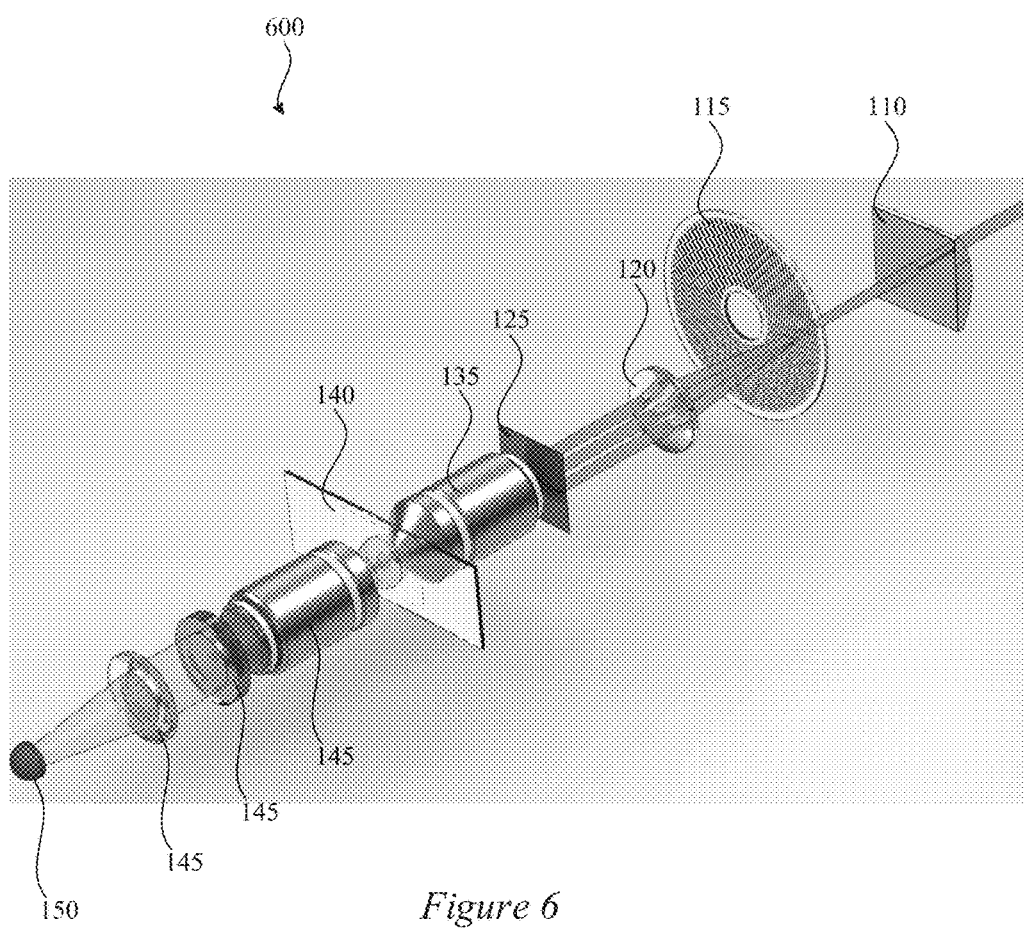
FIG. 6 illustrates an imaging system according to some embodiments described within this document.

FIG. 6 illustrates an imaging system 600 according to some embodiments described within this document. The imaging system 600 includes one or more optical elements 110, a modulator 115, an optical element 120, a filter 125, one or more optical elements 135, a sample region 140, one or more optical elements 145, and a detector 150.

Figure 7:
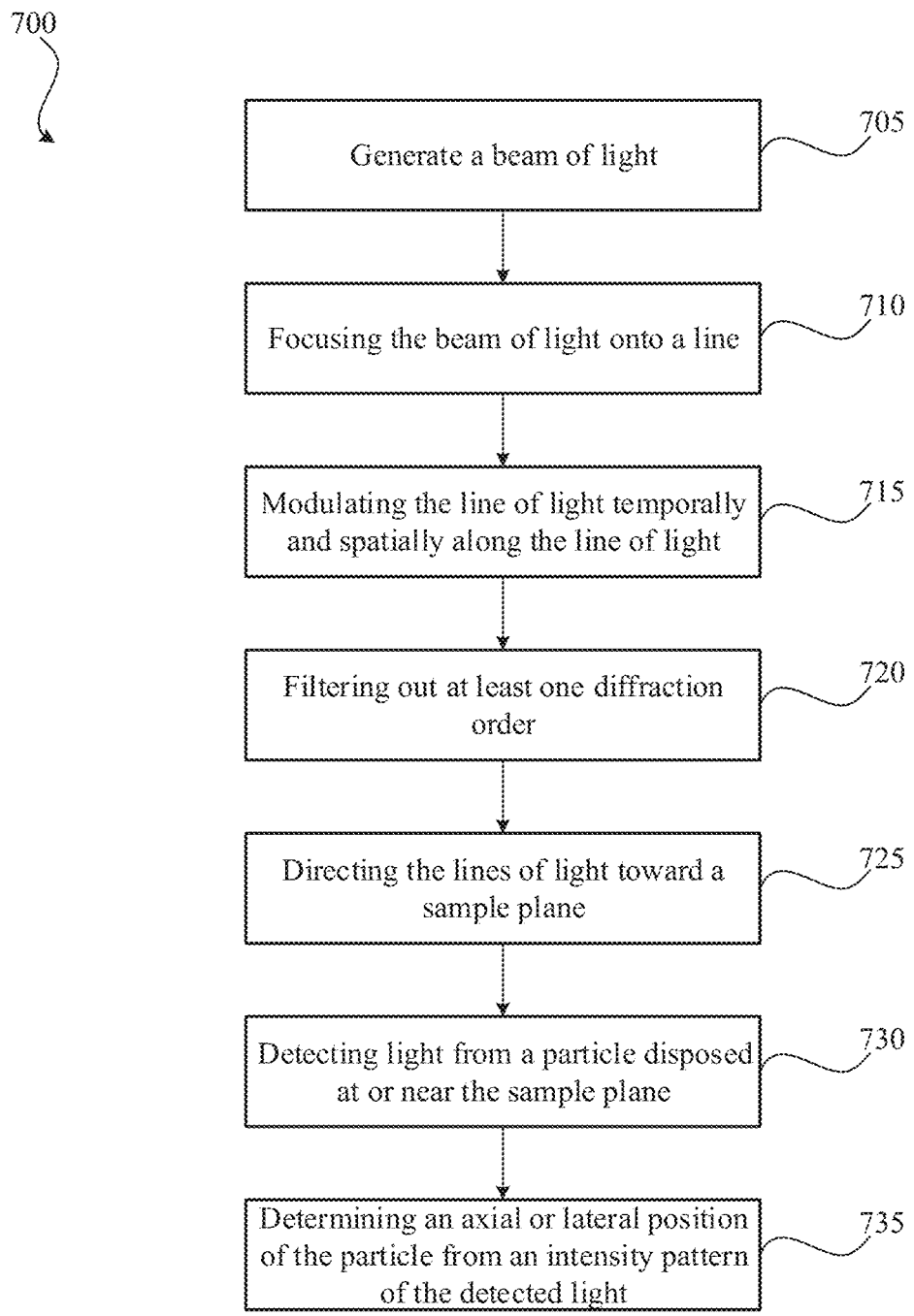
FIG. 7 illustrates a flowchart of a method for determining a lateral or axial position of a particle from a detector signal according to some embodiments.

FIG. 7 illustrates a flowchart of a method for determining a lateral or axial position of a particle from a detector signal according to some embodiments. One or more steps of the method 700 may be implemented, in some embodiments, by one or more components of imaging system 100 of FIG. 1. Although illustrated as discrete blocks, various blocks may be divided into additional blocks, combined into fewer blocks, or eliminated, depending on the desired implementation.

Method 700 begins at block 705 where a beam of light is generated. In some embodiments, the beam of light may be generated using the light source 105 shown in FIG. 1. In some embodiments, the beam of light may be coherent. In some embodiments, the light source may include a laser such as, for example, a continuous wave laser, a pulsed laser, a chirped laser, etc. In some embodiments, the light source may produce light having a wavelength that is tuned to fluoresce a sample disposed within a sample region.

At block 710 the beam of light may be focused into a line of light that extends laterally. In some embodiments, the beam of light may be focused onto a line using any type of optical element such as, for example, optical element 110 and/or a cylindrical lens.

At block 715 the line of light may be modulated by a modulator such as, for example, modulator 115. In some embodiments, the line of light may be modulated both spatially and temporally along the length of the line of light. In some embodiments, the temporal and/or spatial modulation for each point on the line of light during a given time within a time period of the modulator 115 may be unique. For example, intensity of light at each point on the line of light may be different for each point on the light and for each period of time. When a rotating disk is used as the modulator 115, the period of time may be a single rotation period of the modulator 115. In some embodiments, at least three beams of light (e.g., line of light beams) (e.g., 205, 210, and 215) may be produced by the modulator during modulation. In some embodiments, two of the beams of light 205 and 215 may be first-order diffraction beams of light.

At block 720 at least one of the beams of light may be filtered out or blocked using the filter 125. In some embodiments, only two beams of light may pass through the filter 125. In some embodiments, an undiffracted beam of light and a first-order beam of light may pass through the filter.

At block 725 the beams of light, which may be lines of light, may be directed toward the sample region 140. In some embodiments, the undiffracted beam of light 210 and the first-order beam of light 205 may be directed to interfere at or near the sample region 140. Light from a particle(s) disposed at or near the sample region may be illuminated with the beams of light. In response, the particle(s) may emit light having an intensity that is proportional to the intensity of light illuminating the particle(s).

At block 730 the light emitted from the particle(s) may be detected using a detector 150. At block 735 the axial position and/or the lateral position of the particle(s) may be determined from a time series signal of the light detected at block 730.

Figure 8:
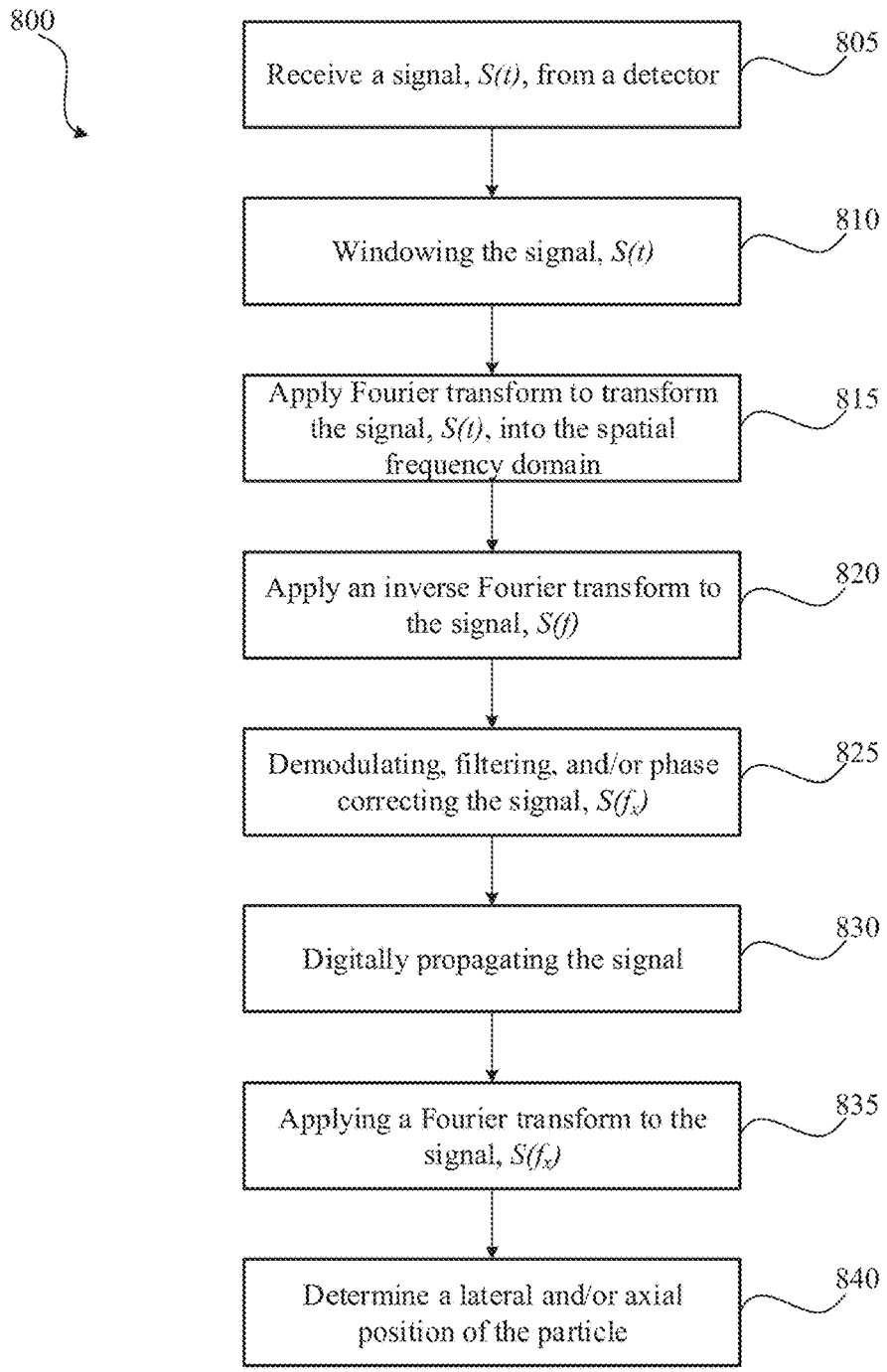
FIG. 8 illustrates a flowchart of a method for determining a lateral or axial position of a particle from a detector signal according to some embodiments.

FIG. 8 illustrates a flowchart of a method 800 for determining a lateral or axial position of a particle from a detector signal according to some embodiments. One or more steps of the method 800 may be implemented, in some embodiments, by one or more components of the processing unit 155 of FIG. 1. Although illustrated as discrete blocks, various blocks may be divided into additional blocks, combined into fewer blocks, or eliminated, depending on the desired implementation.

FIG. 9 illustrates figures or graphs representing data produced in some of the blocks of method 800.

The method 800 begins at block 805 where a time series signal, S(t), is received from the detector 150. In some embodiments, the time series signal, S(t), is proportional to the intensity of light emitted from a particle disposed at or near the sample region. An example signal, S(t), is shown in FIG. 9A.

At block 810 the signal, S(t), may be windowed. In some embodiments, the signal, S(t), may be windowed using a 2D Hann window function.

At block 815 a Fast Fourier Transform may be applied to the signal, S(t), producing a spectral density of the signal, S(f). An example spectral density of the signal, S(t), is shown in FIG. 9B. In FIG. 9B two conjugate line images in the temporal frequency domain, $f_t$, are shown that are centered on the positive and negative carrier modulation frequency, $f_o$, which is applied to the beam by the modulator. The image at $a_r+f_o$ may be isolated by setting all data points outside the image bandwidth to zero.

At block 820, an inverse Fast Fourier transform may be applied to the signal, S(f), in the frequency domain, which may produce a temporal domain signal, wherein f is the modulation frequency. An example of a temporal domain signal is shown in FIG. 9C.

At block 825, the signal S(t) may be processed using one or more signal processing steps such as, for example, demodulation, modulation, filtering, and/or phase correction. For example, the signal $S(f_x)$ may be demodulated by the carrier frequency to remove the linear phase. In some embodiments, various phase disturbances may be removed such as, for example, systematic aberration phase, or pupil phase, and/or the disk aberration phase may be removed from the signal $S(f_x)$. An example of a signal that has undergone demodulation and signal processing is shown in FIG. 9D.

In some embodiments, the signal $S(f_x)$ may be converted from the temporal domain to the lateral spatial frequency domain, $f_x$, which may be directly proportional to one another:

$$f_x = \left(\frac{n_0}{n_m}\right) M \kappa t.$$

The amplitude and phase are plotted as a function of $\lambda f_x$, which may be the numerical aperture (NA).

At block 830, the processed signal $S(f_x)$ may be digitally propagated into a two dimensional signal $S(f_x;\Delta z)$. For example, the signal $S(f_x)$ may be digitally propagated using Ewald Phase. FIG. 9E illustrates the phase of the digitally propagated signal $S(f_x)$ as a function of defocus. In some embodiments, the amplitude of the digitally propagated signal $S(f_x)$ is constant as a function of defocus.

At block 835, a Fast Fourier Transform may be performed on the digitally propagated signal $S(f_x)$ with respect to the lateral spatial frequency domain. The result of the Fast Fourier Transform may produce a numerically reconstructed image in a two-dimensional image in space (e.g., (x, z)). FIG. 9F illustrates an example of the reconstructed image. FIG. 9G illustrates an average of 20 samples, which, for example were not propagated but measured as a function of defocus. Note the fidelity between the image in FIG. 9F and the image in FIG. 9G.

At block 840 the axial and/or lateral position of the particle in the sample region may be determined from the two-dimensional image created at block 835.

In some embodiments, a one-dimensional line image of the lateral dimension may be returned by demodulating the signal, S(t), received from the detector. For example the signal, S(t), may be demodulated by the average frequency. In some embodiments, the scan time can be converted to lateral spatial frequency via $f_x=nM\kappa t$ and a Fourier transform may be computed with respect to $f_x$. The resulting signal may be a one dimensional line image of the lateral dimension.

Figure 10A:
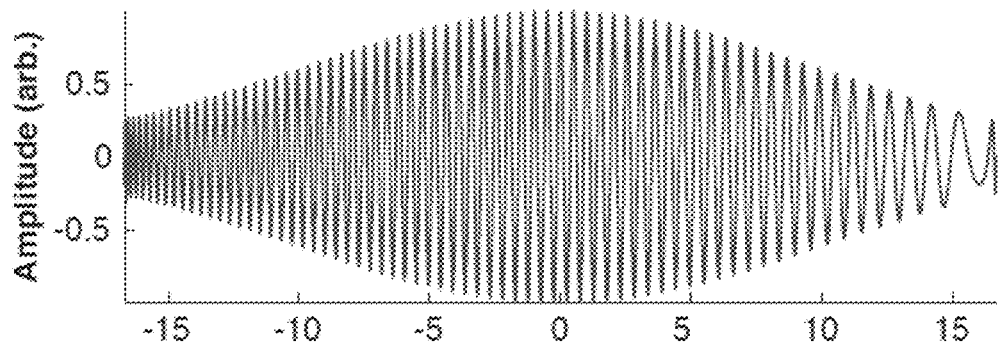
FIGS. 10A and 10B illustrate a comparison of instantaneous modulation frequency between two positions of an emitter in the sample region.
Figure 10B:
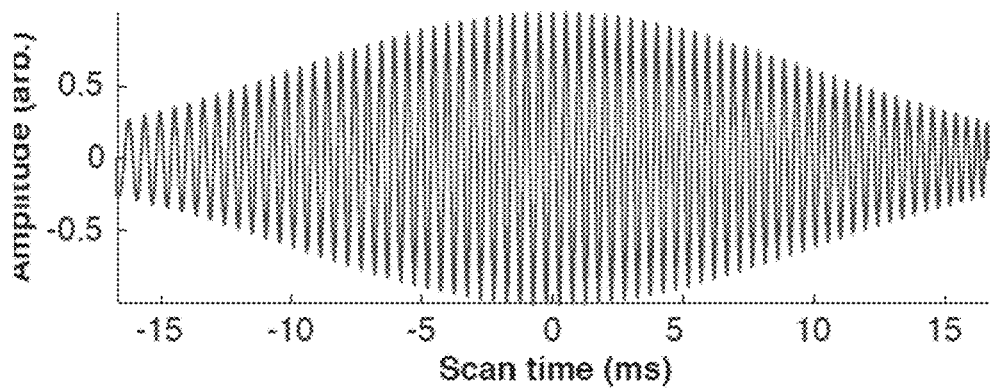

In some embodiments, other numerical functions could be used to numerical transform the signal from the detector to produce a two in a two-dimensional image in space (e.g., (x, z)). FIG. 10A and FIG. 10B illustrate a comparison of instantaneous modulation frequency between two positions of an emitter in the sample region.

Figure 11A:
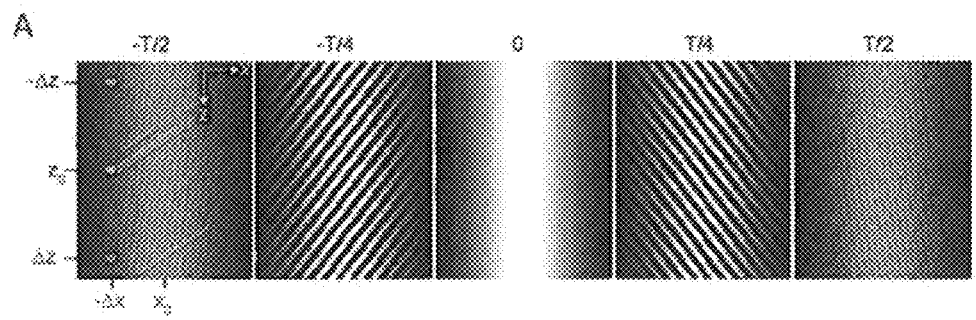
FIGS. 11A-11F illustrate intensity modulation patterns over scan time that are unique for all points in the (x,z) plane and/or determined using various embodiments described in this document and/or the drawings.

FIG. 11A illustrates five example illumination intensity patterns for various times during a full scan of a modulation disk. The parameter T represents the period of the scan.

Figure 11B:
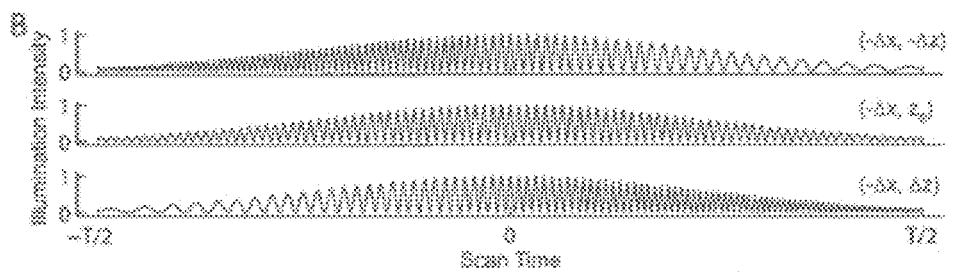

FIG. 11B illustrates three graphs of illumination intensities from a three particles disposed at three different points having the same lateral shift and varying magnitude and sign of defocus (different axial shift).

Figure 11C:
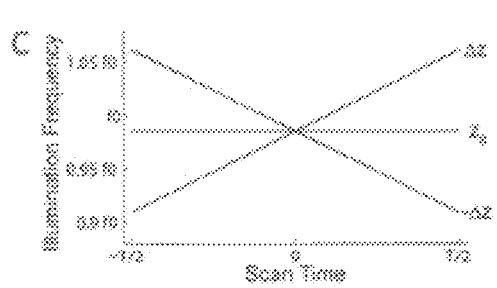

FIG. 11C illustrates three graphs of the instantaneous frequencies of the three particles disposed at the three different points having the same lateral shift and varying magnitude and sign of defocus (different axial shift).

Figure 11D:
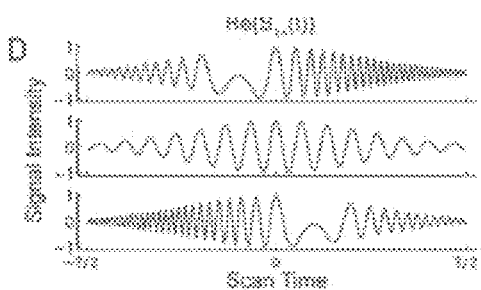

FIG. 11D illustrates three graphs of the amplitude of the temporal first harmonic of the photodetector signal for point emitters disposed at the three different points having the same lateral shift and varying magnitude and sign of defocus (different axial shift)

Figure 11E:
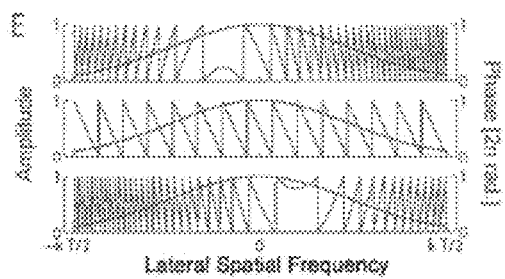

FIG. 11E illustrates three graphs of the amplitude and phase in the lateral spatial frequency domain calculated from the temporal first harmonic detector spectrum using various embodiments described within this document or shown in the figures. The amplitude and/or phase, for example, may be recovered by demodulating the signals in by the carrier frequency and/or substituting $$f_x = \frac{n_o}{n_m} M \kappa t.$$

Figure 11F:
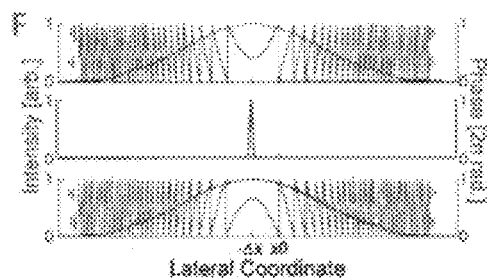

FIG. 11F illustrates three graphs of the intensity and phase for each emitter in real space. The graphs shown in FIGS. 11A-11F were generated using the paraxial theory.

The computational system 1200 (or processing unit) illustrated in FIG. 12 can be used to perform and/or control operation of any of the embodiments described herein. For example, the computational system 1200 can be used alone or in conjunction with other components. As another example, the computational system 1200 can be used to perform any calculation, solve any equation, perform any identification, and/or make any determination described here.

The computational system 1200 may include any or all of the hardware elements shown in the figure and described herein. The computational system 1200 may include hardware elements that can be electrically coupled via a bus 1205 (or may otherwise be in communication, as appropriate). The hardware elements can include one or more processors 1210, including, without limitation, one or more general-purpose processors and/or one or more special-purpose processors (such as digital signal processing chips, graphics acceleration chips, and/or the like); one or more input devices 1215, which can include, without limitation, a mouse, a keyboard, and/or the like; and one or more output devices 1220, which can include, without limitation, a display device, a printer, and/or the like.

The computational system 1200 may further include (and/or be in communication with) one or more storage devices 1225, which can include, without limitation, local and/or network-accessible storage and/or can include, without limitation, a disk drive, a drive array, an optical storage device, a solid-state storage device, such as random access memory ("RAM") and/or read-only memory ("ROM"), which can be programmable, flash-updateable, and/or the like. The computational system 1200 might also include a communications subsystem 1230, which can include, without limitation, a modem, a network card (wireless or wired), an infrared communication device, a wireless communication device, and/or chipset (such as a Bluetooth® device, a 802.6 device, a WiFi device, a WiMAX device, cellular communication facilities, etc.), and/or the like. The communications subsystem 1230 may permit data to be exchanged with a network (such as the network described below, to name one example) and/or any other devices described herein. In many embodiments, the computational system 1200 will further include a working memory 1235, which can include a RAM or ROM device, as described above. The computational system 1200 also can include software elements, shown as being currently located within the working memory 1235, including an operating system 1240 and/or other code, such as one or more application programs 1245, which may include computer programs of the invention, and/or may be designed to implement methods of the invention and/or configure systems of the invention, as described herein. For example, one or more procedures described with respect to the method(s) discussed above might be implemented as code and/or instructions executable by a computer (and/or a processor within a computer). A set of these instructions and/or codes might be stored on a computer-readable storage medium, such as the storage device(s) 1225 described above.

In some cases, the storage medium might be incorporated within the computational system 1200 or in communication with the computational system 1200. In other embodiments, the storage medium might be separate from the computational system 1200 (e.g., a removable medium, such as a compact disc, etc.), and/or provided in an installation package, such that the storage medium can be used to program a general-purpose computer with the instructions/code stored thereon. These instructions might take the form of executable code, which is executable by the computational system 1200 and/or might take the form of source and/or installable code, which, upon compilation and/or installation on the computational system 1200 (e.g., using any of a variety of generally available compilers, installation programs, compression/decompression utilities, etc.), then takes the form of executable code.

The goal of this section is to calculate the form of the signal collected on a photodetector. Assuming coherent illumination of the spatial temporally varying modulation mask. Some embodiments encode complex spatial image information into a temporal intensity measurement by spatially integrating the radiant flux from the contrast distribution on a single-element photodetector as the illumination intensity pattern is modulated over time. The signal may have the form:

$$S(t) = \int_{-\infty}^{\infty} d^3r I(r,t) C(r,t),$$

where $I(r, t)$ is the illumination pattern in the sample region, and $C(r, t)$ is the contrast distribution. The contrast distribution describes the method by which illumination intensity is transferred to contrast intensity. For example, the contrast distribution can simply represent the transmittance of the object if the measured contrast intensity is the illumination source after propagation through an object displaying absorption. In that case, $C(r,t) = \mathbb{T}(r,t) = 1 - \mathbb{A}(r,t)$, where $\mathbb{T}$ is the intensity transmission of the object, and $\mathbb{A}$ is the intensity absorption of the object, and an image is formed from the object transmission. The contrast can also represent the spatial concentration distribution of fluorophores in an object, scaled by absorption cross section for the excitation light and efficiency of fluorescent emission. Throughout this analysis, it shall be assumed that the contrast function is constant for the duration of a scan, so that $C(r,t) \to C(r)$. It shall also be assumed that the contrast function is linearly proportional to the illumination intensity.

The propagation phase imparted to the contrast intensity arises from a change in the modulation frequency at a given point in the contrast distribution as a function of scan time. In general, the spatial phase of the illumination source is encoded in the signal from the photodetector as a phase variation on the temporal carrier frequency.

To derive the form of the signal from the photodetector, a plane wave expansion of the incident line focus on the modulator mask may be considered that may be generated by a set of transverse wave vectors induced by spatial temporal modulations arising from diffraction from the modulator. An expression for the electric field diffracted from the modulation mask for an arbitrary set of diffracted fields can be calculated. The magnification of the imaging system may then be applied, and the phase accumulated with propagation using an angular spectrum formalism applied to the reimaged diffracted waves may be calculated. An expression for the total illumination field in the sample region is found by summing all of the diffracted orders, which is used to compute the final illumination intensity distribution in the sample region. With the first order nontrivial approximation and/or a Fresnel approximation equivalent to defocus aberration, an analytic expression for the illumination intensity that includes the effects of the quadratic defocus phase can be found.

The set of k-vectors and spatial coordinates are described with an arbitrary position vector, $r = x\hat{e}_x + y\hat{e}_y + z\hat{e}_z$, and wavevector, $k = k_x\hat{e}_x + k_y\hat{e}_y + k_z\hat{e}_z$. The optic axis of the system is set to be the z-direction ($\hat{e}_z$), and transverse k-vectors may be defined (in the x-y plane) by the notation $k_\perp = k_x\hat{e}_x + k_y\hat{e}_y$, and the position in the transverse plane as $r_\perp = x\hat{e}_x + y\hat{e}_y$.

For simplicity it may be assumed that a uniform plane wave of unit amplitude incident on a diffraction mask, and propagating along the optic axis, which is normal to the plane that defines the diffraction mask. The incident field contains a single spatial frequency so that the electric field incident on the modulation mask can be written as $$E_{inc}(r) = e^{ik_{in} \cdot r} = e^{ik_{in} z},$$

where $k_{in} = 2\pi/\lambda$ is the wavenumber of the incident wave and the wave vector is strictly along z, $k_{in} = k_{in}\hat{e}_z$.

Since the source is spatially coherent, the modulation mask causes the incident field to diffract into multiple directions propagating at various angles with respect to the optic axis. The structure of the mask dictates the direction of the diffracted wave vectors by imparting a transverse wavevector to the incident plane wave. Expressing the magnitude of the k-vector in the transverse plane (x, y) of a diffracted field j as $k_{\perp,j}$ the axial k-vector for each diffracted wave is:

$$k_{z,j} = \sqrt{k_0^2 - k_{\perp,j}^2} = k_0 n \sqrt{1 - \left(\frac{Mk_{\perp,j}}{k_0 n}\right)^2}$$

where the subscript $\perp$ indicates the vector components in the transverse plane. In some embodiments, the small angle approximation, e.g., $(k_{\perp,j}^2/k_0^2) \ll 1$, can be utilized to simplify the expression. Note that the resulting phase is simply the Fresnel approximation of the propagation phase. The electric field for the $j^{th}$ diffracted wave is:

$$E_j(r) = a_j e^{ikj \cdot r} = a_j e^{ik_{\perp,j} \cdot r_\perp} e^{ik_{z,j} z}$$

The electric field distribution directly behind the modulator is image relayed to the sample region with an imaging system of magnification M. Denoting the image of the $j^{th}$ diffracted field in the sample region with the subscript j', the axial wave-vector in the sample region is:

$$k_{z,j'} = \sqrt{k_{j'}^2 - k_{\perp,j}^2} = k_0 \sqrt{1 - \left(\frac{Mk_{\perp,j}}{k_0 n}\right)^2}$$

where $k_{\perp,j'} = Mk_{\perp,j}$. Thus the electric field for the $j^{th}$ diffracted wave in the sample region becomes:

$$E_{j'}(r) = a_{j'} e^{ik_{\perp,j'} \cdot r_\perp} e^{ik_{z,j'} z} \approx a_{j'} e^{ik_{\perp,j'} \cdot r_\perp} \exp\left[ik_0 nz \sqrt{1 - \left(\frac{Mk_{\perp,j}}{k_0 n}\right)^2}\right]$$

For the intensity transmission masks, which are positive semi definite each diffraction angle possesses a positive and negative pair of angles, so that we need to account for diffracted waves at $\pm k_{\perp,j}$. A given mask can generate many diffracted waves, which can either be derived from higher diffracted orders of a particular mask lattice vector, or from the inclusion of multiple lattice vectors that can diffract beams to additional angles. If we suppose that we have a total of N diffracted waves of appreciable power, then we have a total of 2N+1 waves (including the zero-order term) that must be accounted for. The total illumination field propagating in the sample region can thus be compactly expressed as $$E_{ill}(r) = \sum_{j'=-N}^{N} E_{j'}(r) = a_0 e^{ik_0 z} + \sum_{j' \neq 0} a_{j'} e^{ik_{\perp,j'} \cdot r_\perp} e^{ik_{z,j'} z}$$

Because the mask is real and positive semi definite, all of the diffracted waves for given index j, have equal amplitude and conjugate, i.e., $a^*_{-j} = -a^*_j$. Incorporating this condition with the Fresnel approximation, the electric field in the sample region can be simplified to read:

$$E_{ill}(r) = a_0 e^{ik_0 z} + \sum_{j \neq 0} a_j e^{iMk_{\perp,j} \cdot r_\perp} \exp\left[ik_0 z \sqrt{1 - \left(\frac{Mk_{\perp,j}}{k_0 n}\right)^2}\right]$$

Each pair of diffracted waves ±j' have the same axial wave vector, but conjugate transverse wave vectors, so conjugate pairs in the summation can be paired:

$$E_{ill}(r) = a_0 e^{ik_0 z} + \sum_{j=1}^{N} |a_j| \cos(Mk_{\perp,j} \cdot r + \angle a_j) \exp\left[ik_0 z \sqrt{1 - \left(\frac{Mk_{\perp,j}}{k_0 n}\right)^2}\right]$$

The intensity in the sample region is the square modulus of the expression above, $I_{ill}(r) = |E_{ill}(r)|^2$.

Utilizing Eq. (10), which has been propagated with the Fresnel approximation, the illumination intensity in the object region for an arbitrary modulation mask can be found by calculating the set of transverse wave vectors, $\{k_{\perp,j}\}$, imparted by the mask. To obtain an expression for the transverse wave-vectors, the mask as a decomposition of plane wave vectors may be considered. It can be assumed that the mask is constructed of periodic modulations along directions described by lattice vectors $\hat{e}_p$. It can be assumed that the mask modulates the amplitude of the field, requiring that it be positive semi definite. With both of these assumptions in hand the general form of the mask as a Fourier cosine decomposition of wave vectors can be written:

$$m(r) = \sum_{p=-\infty}^{\infty} a_p \cos(k_p \cdot r) = a_0 + \sum_{p \neq 0} a_p \cos(k_p \cdot r)$$

The term $a_0$ is simply a constant offset that must be selected to allow the mask to be positive semi definite. All other terms correspond to periodic patterns in the modulation mask. Assuming that the amplitude of the mask is unity and that each diffracted component has the same amplitude, $a_p = (1-a_0)/N$, yielding a mask expansion given by:

$$m(r) = a_0 + \frac{1-a_0}{N} \sum_{p=1}^{N} \cos(k_p \hat{e}_p \cdot r)$$

where the fact that $k_p = k_p \hat{e}_p$ has been utilized. Since the modulation mask is confined to the lateral plane, i.e., the mask has no axial modulations, this wave vector is equivalent to the transverse wave vector experienced by the incident electric field. Therefore, $k_p = k_{\perp,j}$ and a general expression for the modulation mask has been arrived at in terms of the lateral wave vectors imparted onto the incident coherent illumination source:

$$m(r) = a_0 + \frac{1-a_0}{N} \sum_{p=1}^{N} \cos(k_{\perp,j} \cdot r) = a_0 + \frac{1-a_0}{N} \sum_{p=1}^{N} \cos(k_{\perp,j} \hat{e}_j \cdot r)$$

In polar coordinates, the pattern of a modulation mask has the form:

$$m(R,\theta) = \frac{1}{2} + \frac{1}{2} \operatorname{sgn}[\cos(\Delta k R \theta)]$$

where sgn[·] is included to account for the binary amplitude modulation resulting from the printing process.

In Cartesian components, $\hat{x}$ is the lateral dimension, parallel to the line focus, and $\hat{y}$ is the vertical direction, perpendicular to the line focus. The region sampled by the line focus, located at y=0, and approximately centered on one side of the mask such that the illumination distribution in x lies between the inner and outer radii of the mask is of interest. To account for the changing modulation pattern sampled by the line focus during mask rotation, and thus find the local spatial frequencies as a function of scan time, the mask may be considered:

$$m(R,\theta-\theta_0) = \frac{1}{2} + \frac{1}{2} \operatorname{sgn}\{\cos[\Delta k R(\theta-\theta_0)]\}$$

where $\theta_0$ describes the rotation angle of the mask. Since the mask rotates at a constant angular velocity, $\theta_0 = 2\pi f_r t$, where $f_r$ is the angular frequency of the mask.

To uniquely determine the spatial phase of the illumination microscope, only the first diffracted order from the mask is permitted to interfere with the undiffracted beam in the sample region. Higher diffracted orders resulting from the binary modulation scheme are omitted in the following analysis, and also excluded in some embodiments so that the mask may be considered as:

$$m(R, \theta - \theta_0) = \frac{1}{2} + \frac{1}{2} \cos[\Delta k R(\theta - \theta_0)] = \frac{1}{2} + \frac{1}{2} \cos[\phi(R, \theta_0)]$$

The local linear spatial frequency imparted by the mask in Cartesian coordinates is:

$$f_x = \frac{1}{2\pi} \frac{\partial \phi(r, \theta)}{\partial x}$$

$$f_y = \frac{1}{2\pi} \frac{\partial \phi(r, \theta)}{\partial y}$$

The local region sampled by the beam is along the line where $\theta=0$, so the local angular spatial frequencies can be calculated as:

$$k_x = \left[\cos\theta \frac{\partial \phi(r, \theta)}{\partial r} - \frac{1}{r}\sin\theta \frac{\partial \phi(r, \theta)}{\partial \theta}\right]_{\theta=0}$$

$$k_y = \left[\cos\theta \frac{\partial \phi(r, \theta)}{\partial r} + \frac{1}{r}\cos\theta \frac{\partial \phi(r, \theta)}{\partial \theta}\right]_{\theta=0}$$

where the linear spatial frequency has been converted to angular spatial frequency by multiplying by $2\pi$. The local spatial frequencies evaluate to:

$$k_{x,1} = 2\pi\Delta k f_r t \equiv 2\pi\kappa t$$

and $$k_{y,1} = \Delta k$$

In the lateral dimension, spatio-temporal modulations encode the lateral position with unique modulation frequencies. Moreover, each measurement in time corresponds to a unique lateral spatial frequency.

In the vertical dimension, a constant, non-zero spatial frequency separates the positive and negative diffracted orders, allowing for a spatial filter to be placed in a Fourier plane of the mask to select only one diffracted order. This removes the ambiguity of sign in the accumulated spatial phase, and allows unique measurement of the spatial phase difference between the undiffracted and diffracted illumination beams.

Returning to the general form of the modulation mask, the transverse wave-vector can be decomposed into Cartesian components to give:

$$m(x, y, t) = \frac{1}{2} + \frac{1}{2N} \sum_{p=1}^{N} \cos(2\pi\kappa t x + \Delta k y)$$

where set $a_0 = \frac{1}{2}$. Only one of the first order diffracted modes may be utilized and the undiffracted beam, the plane wave expansion of the mask can be simplified further:

$$m(x,y,t) = \frac{1}{2} + \frac{1}{2}\cos(2\pi\kappa t x + \Delta k y)$$

The illumination intensity pattern may be formed by allowing only one of the diffracted orders to interfere with the undiffracted beam in the sample region. This may be accomplished with a horizontally oriented slit placed near the pupil plane of the illumination lens that passes only a portion of the $j=0$ and $j=1$ or $j=-1$ orders, which is possible due to a non-zero spatial frequency component in the vertical ($\hat{e}_y$) direction that is independent of the rotation angle of the mask. Including only the positive diffractive ($j=+1$) and zero ($j=0$) orders, the illumination field is:

$$E_{ill}(r, t) = \frac{1}{2}e^{ink_0 z} + \frac{1}{4}\exp[iM(2\pi nM\kappa t x + \Delta k y)] \times$$

$$\exp\left\{ik_0 nz\left[1 - (\lambda M\kappa t)^2 - \left(\frac{\lambda M\Delta k}{2\pi}\right)^2\right]\right\}e^{i\Phi_{pupil}(t)}$$

The illumination intensity is the square modulus of the expression above:

$$I(r, t) = \frac{5}{16} + \frac{1}{4}\cos\left\{2\pi(nM\kappa t)x + (nM\Delta k)y + \right.$$

$$\left. k_0 nz\left[\sqrt{1 - (\lambda M\kappa t)^2 - \left(\frac{nM\Delta k}{2\pi}\right)^2} - 1\right] + \Delta\Phi_a(t)\right\},$$

wherein $\Delta\Phi_a(t) \equiv \Phi_{pupil}(2\pi\kappa t) - \Phi_{pupil}(0)$

In some embodiments, the illumination system was designed to allow portions of the $j=0$ and $j=1$ beams to pass at the equator of the objective lens (vertically), thereby removing the shear between the diffracted and undiffracted beams in the vertical dimension. As such, one can make the approximation that in the sample region, $\Delta k \to 0$ in the y-direction only, and the illumination intensity pattern no longer varies with respect to the vertical dimension:

$$I_{filtered}(x, z; t) =$$

$$\frac{5}{16} + \frac{1}{4}\cos\left\{2\pi(nM\kappa t)x - k_0 nz\left[\sqrt{1 - (\lambda M\kappa t)^2 - \left(\frac{nM\Delta k}{2\pi}\right)^2} - 1\right]\right\}.$$

The spatio-temporal illumination intensity encodes each lateral axial position in the sample region by imparting a unique illumination pattern over the duration of the scan. Several properties of this illumination are worth noting.

First, it can be noted that the illumination intensity pattern has temporal dependence that varies in x and z, but not in the vertical, y, coordinate. This is expected as the vertical spatial frequency on the modulation mask is constant with respect to time because it is invariant with mask rotation angle, $\theta$. The effect of the vertical spatial frequency is to impart a linear phase delay in the vertical dimension that is directly proportional to the mask density, $M\Delta k$, and another linear phase delay with respect to the optic axis that arises from the shear of the re-imaged diffracted order. The linear phase delay leads to an intensity modulation in the case where the full y spatial frequency extent of the zero-order and first diffracted order beam is allowed to pass through the illumination optical system. Placement of the filter that selects a portion of the y spatial frequency content eliminates this modulation that arises from the vertical spatial frequency shear. The presence of the restrictive spatial filter leads to the illumination intensity distribution, where it is evident that this filtered illumination intensity lacks any modulation dependence along the y-direction, and yet retains a temporal modulation intensity that varies with both x and z. This behavior follows from the fact that a portion of the zero-order and first diffracted order are selected in a Fourier plan, so that no y-spatial frequency offset is retained after the spatial filtering operation. This filtered illumination intensity allows the intensity illuminating the sample region to vary with time in the lateral and axial direction, and thus each point in time represents a unique illumination intensity in the (x, z)-plane, while the illumination intensity in the vertical dimension is constant during the scan, depending only on the properties of the modulation mask and imaging optics.

Second, the illumination intensity can be thought of as a background (DC) component that is constant with time, and a temporally-varying (AC) component, which may be written as $I_0(r)$ and $I_1(r,t)$ respectively. The AC component is responsible for encoding the image into the temporal measurement. The measured signal as a sum of the AC and DC components can be written as:

$$S(t) = \int_{-\infty}^{\infty} d^3r [I_0(r) + I_1(r,t)] C(r) = S_0(t) + S_1(t)$$

The first harmonic of the temporal signal, $S_1(t)$ encodes the image.

Finally, since only the lateral and axial components of the contrast function are encoded into the temporal signal, It can be assumed that the contrast function is separable with respect to the vertical dimension, i.e., $C(r) = C_y(y) C(x,z)$, so that the AC signal is:

$$S_1(t) = \tfrac{1}{4} w(t) \int_{-\infty}^{\infty} dy \; C_y(y) \iint_{-\infty}^{\infty} dz dx \; C(x,z) \times \cos\{2\pi(nM\kappa t)x + k_0 nz[\sqrt{1-(\lambda M\kappa t)^2}-1]\}$$

Integration over the vertical coordinate in the expression above results in a constant multiplicative factor. Let us define an overall prefactor to account for this integration and the leading factor of ¼ as $\gamma \equiv (\tfrac{1}{4})\int dy C_y(y)$.

These equations may represent the signal collected from the photodetector, which must be real-valued and it follows that the signal displays conjugate spectral symmetry. Both the positive and negative fundamental modulation sidebands encode the defocus phase information, although they are conjugates to one another. For image reconstruction, only one such signal is needed. The complex spatial frequency spectrum from the temporal data trace is isolated by filtering out the positive frequency sideband of the frequency of the measured signal, then inverse transformed. After these operations, an expression for the measured spatial frequency distribution can be arrived at; the amplitude of the time-dependent trace contains the object intensity spatial frequency distribution, and the phase of represents the propagation and modulation phase of the illumination intensity accumulated between the modulator and the sample region. In the analytic theory presented here, this is readily observed by representing the cosine term as a sum of complex exponentials:

$$S_1(t) = \tfrac{1}{2} w(t) \gamma \iint_{-\infty}^{\infty} dz dx C(x,z) \{\exp[i2\pi(nM\kappa t)x + k_0 nz(\sqrt{1-(\lambda M\kappa t)^2}-1) + i\Delta\Phi_a(t)] + c.c\}$$

where c.c. denotes the complex conjugate. The positive and negative temporal sidebands centered at $\pm f_0$ can be represented as $S_{1+}(t)$ and $S_{1-}(t)$ respectively, such that $S_1(t) = S_{1+}(t) + S_{1-}(t)$. In practice, the positive temporal first harmonic can be selected for image reconstruction. Re-normalizing the AC signal by the prefactor $\gamma$ in an expression for the image from a single lateral-axial plane can be arrived at:

$$S_{1+}(t) = \iint_{-\infty}^{\infty} dz dx \exp[i2\pi(nM\kappa t)x - k_0 nz[1-(\lambda M\kappa t)^2 - 1] + i\Delta\Phi_a(t)] C(x,z)$$

It is instructive to rewrite this expression in terms of the lateral and axial integrals as:

$$S_{1+}(t) = w(t) e^{(i2\pi v_c t)} e^{i\Delta\Phi_a(t)} \int_{-\infty}^{\infty} dz e^{ik_0 n\Delta z[\sqrt{1-(\lambda M\kappa t)^2}-1]} \times \int_{-\infty}^{\infty} dx C(x,z) e^{i2\pi(nM\kappa t)\Delta x}$$

where the substitution $z \rightarrow (z-z_0)$ has been made where $z_0$ is the axial location of the focal plane, and $x \rightarrow (x+x_0)$, where $x_0$ is the lateral location of the center of the image. The carrier frequency, $f_0$, is the frequency corresponding to $x_0$, and is defined as $f_0 = M\kappa x_0$.

From the local spatial frequency calculation, the lateral spatial frequency imparted by the mask, $f_x$, is:

$$f_x = \frac{n_o}{n_m} \frac{k_x}{2\pi} = \frac{n_o}{n_m} M\kappa t.$$

Upon re-imaging of the mask plane to the sample region, the local lateral spatial frequency is increased by a factor of M, such that in the sample region the spatial frequency becomes $M\kappa t$. Therefore, the temporal first harmonic of the signal in the lateral spatial frequency domain as:

$$S_{1+}(f_x) = w(f_x) e^{i2\pi f_x x_0} e^{i\Delta\Phi_a(f_x)} \int_{-\infty}^{\infty} dz e^{ik_0 n\Delta z\left[\sqrt{1-\left(\tfrac{\lambda}{n} f_x\right)^2}-1\right]} \times \int_{-\infty}^{\infty} dx C(x,z) e^{i2\pi f_x x}$$

These equations demonstrate how amplitude and phase information from the spatial frequency domain are encoded into a temporal measurement. By virtue of the phase delay with respect to the carrier frequency, $f_0$, in the signal, the total spatial phase accumulated between the modulation plane and the sample region is encoded into a single temporal measurement. This includes phase variation from defocus, which is explicitly included in the theory presented above, as well as higher-order spatial frequency phase variations. It is clear that the temporal first harmonic of the photodetector signal encodes lateral position through carrier frequency, and axial position through frequency chirp, corresponding to linear and quadratic spatial phase respectively. Note that the defocus phase manifests in the form of a Fresnel zone plate (FZP) in the lateral spatial frequency domain.

The complex signal may be the positive exponential component of a real harmonic with oscillation frequency. And the signal may encode the spatial location of the point emitter through the instantaneous oscillation frequency measured on the photodetector. The instantaneous oscillation frequency of the measured signal is $$v(t) = \frac{\partial}{\partial t}\left\{\frac{\Delta\phi(x_p, z_p, t)}{2\pi}\right\} =$$

$$\frac{\partial}{\partial t}\left\{\frac{\Delta OPL(x_p, z_p, t)}{\lambda}\right\} = v_c + nM\kappa x_p - \frac{n\lambda(M\kappa)^2 t}{\sqrt{1-(\lambda M\kappa t)^2}} z_p + \frac{1}{2\pi}\frac{\partial \Delta\Phi_a(t)}{\partial t}$$

This simple linear relationship between the position of the point emitter and the instantaneous temporal frequency of the measured signal is convenient for understanding how each position has a unique temporal modulation pattern in the sample region. For a collection of $N_p$ point emitters with locations given by a set of coordinates $\{(x_p, z_p)\}$, the contrast function becomes:

$$C(x, z) = \sum_{p=1}^{N_p} \delta(x - x_p)\delta(z - z_p)$$

and the signal from the photodetector is a linear combination of the signals from each emitter.

$$S_{1+}(t) = \sum_{p=1}^{N_p} e^{i2\pi(f_0 - M\kappa x_p)t} e^{-i\pi\lambda(z-z_p)(M\kappa t)^2}$$

Because the total signal is a linear combination, the temporal scan encodes a summation of FZPs in the lateral spatial frequency domain. Uniqueness of the illumination pattern for conjugate locations in the sample region, $(x_1, z_1)$ and $(x_1, -z_1)$, is maintained by the shift in instantaneous frequency relative to the carrier frequency, $f_0$, preventing ambiguity of emitter location in the measured signal. The location of each point emitter is recovered with the same Fourier transform procedure as outlined for a single emitter.

One important advantage of embodiments of the invention is decoupling of lateral spatial resolution and depth of field. In tightly focused imaging techniques, such as laser scanning microscopy, the depth of field and lateral spatial resolution are both set by the NA of the illumination objective. Some embodiments do not suffer this same limitation, as collimated beams are utilized to measure high spatial frequency data. Instead, the depth of focus is defined by the axial distance over which the intensity modulation $h(r,t)$ is supported. In the theoretical analysis thus far, a plane wave illumination has been assumed. This causes both the field of view (FOV) and depth of field (DOF) to be infinite, since the region of finite support for $I_1(r,t)$ tends towards infinity. This is clearly not consistent with the experiment, as the aperture of the illumination system and modulation mask will ultimately limit the extent of the illumination beams in the lateral and vertical dimensions.

Let us assume instead that the illumination beam incident on the modulation mask has a Gaussian intensity profile in the lateral dimension and is collimated in the axial dimension. The incident illumination field may be written as $$E_{inc}(r) = u(x)e^{ik_0 z} = e^{-(x-x_0)^2/w^2} e^{ik_0 z}$$

where w is the width of the Gaussian distribution.

The approximation that upon diffraction from the mask may be applied, the amplitude distribution simply rotates by the diffraction angle. Upon reimaging into the sample region, a coordinate transformation to the amplitude distribution to find that for a given diffracted order may be applied, the amplitude distribution is:

$$u_{j'}(r,t) \approx u_{j'}(x,z,t) = \exp\left\{-\frac{[(x-x_0)\cos(j\lambda M\kappa t) - (z-z_0)\sin(j\lambda M\kappa t)]^2}{(w/M)^2}\right\}$$

Because the signal relies on excitation by the temporal first harmonic of the illumination intensity, $I(r,t)$, the DOF may be written as:

$$DOF_z(t) = \frac{2w}{\lambda M\kappa t} = \frac{2w}{\lambda f_{x,o}(t)}$$

Since the highest spatial frequency that may contribute to the measurement corresponds to the maximal scan times, can be recast in terms of the numerical aperture of the imaging system to find the DOF for the full numerical aperture of the imaging system.

$$DOF_z = \frac{2w}{\lambda M\kappa T/2} = \frac{4w}{\lambda M\Delta\kappa f_r T} = \frac{4w}{\lambda M\Delta k} = \frac{2w}{NA}$$

For the Gaussian illumination beams considered here, the DOF may be limited by the width of the beam incident on the mask, w, the microscope magnification, M, the density of the mask through the relation $\kappa = \Delta k f_r$, and the scan time, t. The effect of the DOF function is to limit the axial region over which data is collected at a given scan time. For $t=0$, the DOF is infinite, since the illumination intensity is defined by two co co-propagating beams. As the magnitude of the scan time increases, the overlap region of the two illumination beams decreases due to the finite width of the illumination beam amplitude. Recalling that the scan time is directly proportional to the lateral spatial frequency, this is equivalent to a limit on the lateral frequency support as a function of axial position. Ultimately this effect is responsible for a loss of lateral spatial resolution in the case of an object lying far away from the focal plane.

In some embodiments, each temporal trace measured may represent a holographic projection through the object, as one expects in analogy with conventional coherent holographic imaging. As such, measurement and reconstruction based on optical diffraction tomography (DT) can be performed by capturing traces for varying incident angles with respect to the specimen.

Consider again the case of a point emitter located in the lateral axial plane. Assigning the laboratory coordinates as (x, z) and the object coordinates as, the analytic contrast function for a point emitter can be expressed in object coordinate space as:

$$C(\xi,\eta) = \delta(\xi - \xi_p)\delta(\eta - \eta_p)$$

In laboratory coordinates, the contrast function is still expressed by $C(x,z) = \delta(x - x_p)\delta(z - z_p)$ Projections are measured in laboratory coordinates as a function of object rotation angle, $\phi$, and are calculated by applying the rotation matrix to find $(x_p, z_p)$ in terms of $(\xi_p, \eta_p)$. The resulting contrast function in laboratory coordinates is:

$$C(x,z) = \delta(x - \xi_p \cos\phi + \eta_p \sin\phi)\delta(z - \xi_p \sin\phi - \eta_p \cos\phi)$$

Inserting this contrast function into the expression for the signal, the temporal photodetector signal can be calculated for a rotation object.

Fortunately, the higher order phase preserved in the measurement can be inverted to digitally correct for residual higher order phase that is responsible for image distortions. Numeric correction of higher order spatial aberrations was performed on selected sets of digitally refocused data.

Aberration correction consisted of removing residual phase after digitally refocusing the data to form a holographic reconstruction. The non-defocus (non-quadratic) spatial phase was removed by first subtracting the Ewald phase (or subtracting the Fresnel phase) used for propagation from the digitally refocused image. The remaining phase was then inverted and applied to the data to form an aberration-corrected image of the specimen.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art.

That which is claimed:

1. A system comprising:
   a light source that produces a beam of light;
   an optical element that produces a line of light from the beam of light;
   a modulator disposed in an optical path of the line of light that temporally modulates an intensity pattern of the line of light uniquely at each point along a lateral length of the line of light, and produces at least an undiffracted modulated line of light, a first first-order diffracted line of light, and a second first-order diffracted line of light;
   one or more optical elements configured to direct the undiffracted modulated line of light and one of the first first-order line of light and the second first-order line of light toward at least one particle disposed at or near a sample region;
   a single-element photodetector configured to detect light emanating from the particle disposed at or near the sample region; and
   a processor electrically coupled with the single-element photodetector and configured to determine an axial position of the particle disposed at or near the sample region and a lateral position of the particle disposed at or near the sample region based on the intensity pattern of light detected at the single-element photodetector.

2. The system according to claim 1, wherein the intensity pattern varies as a function of time.

3. The system according to claim 1, wherein the one or more optical elements includes a spatial filter having at least a single slit.

4. The system according to claim 1, wherein the modulator comprises at least one of a patterned mask, an acousto-optical modulator, an acousto-optical deflector, and a circular modulation mask.

5. The system according to claim 1, wherein the one or more optical elements direct the undiffracted modulated line of light and one of the first first-order line of light and the second first-order line of light to interfere at or near the sample region.

6. The system according to claim 1, wherein an axial position resolution of the system is decoupled from a lateral position resolution of the system.

7. A system comprising:
   a light source that produces a beam of light;
   a modulator disposed in an optical path of the beam of light that temporally modulates an intensity pattern of the beam of light uniquely at each point along a focus of the beam of light to form an intensity modulation pattern at a sample region that is unique for every spatial location in a lateral-axial plane of the sample region;

one or more optical elements configured to direct light from the modulator toward the sample region;

a detector configured to detect light from the sample region; and a processor electrically coupled with the detector and configured to determine an axial position of a particle disposed at or near the sample region based on a spatio-temporally modulated signal light from the particle that is emitted by the particle responsive to illumination by a portion of the intensity modulation pattern that is unique to a spatial location of the particle and that is detected at the detector.

8. The system according to claim 7, wherein the modulator produces two first-order diffracted beams of light and an undiffracted beam of light, the system further comprising an optical element configured to direct at least one of the two diffracted beams of light and the undiffracted beam of light to interfere at the sample region.

9. The system according to claim 7, wherein the modulator produces two first-order diffracted beam of light and an undiffracted beam of light, and the system further comprising a filter that filters out all but one first-order diffracted beam of light.

10. The system according to claim 7, wherein the modulator modulates a frequency imparted to a line focus that varies linearly with a function of lateral position.

11. The system according to claim 7, wherein the modulator comprises at least one of a patterned mask, an acousto-optical modulator, an acousto-optical deflector, and a circular modulation mask.

12. A method comprising:

producing a line of light with a light source;

modulating the line of light both temporally and spatially along a lateral length of the line of light into modulated light;

directing the modulated light toward a sample region, wherein the modulated light forms an intensity modulation pattern at the sample region that is unique for every spatial location in a lateral-axial plane of the sample region;

detecting, with a light detector, light from at least one particle disposed at or near the sample region; and determining an axial position of the particle from an intensity pattern of the detected light.

13. The method according to claim 12, wherein the light source comprises an optical element comprising either or both a cylindrical lens and an optical element with a slit.

14. The method according to claim 12, wherein the line of light is modulated with at least one of the following devices a patterned mask, an acousto-optical modulator, an acousto-optical deflector, and a circular modulation mask.

15. The method according to claim 12, wherein the modulated light includes at least two diffracted beams of light, and wherein the method further comprises filtering out at least one of the two diffracted beams of light.

16. The method according to claim 12, wherein:

the modulated light includes an undiffracted beam of light and two first-order diffracted beams of light;

the method further comprises filtering out a first one of the two first-order diffracted beams of light and passing through the undiffracted beam of light and a second one of the two first-order diffracted beams of light;

directing the modulated light toward the sample region includes directing the undiffracted beam of light and the second one of the two first-order diffracted beams of light to interfere at or near the sample region.

17. The method according to claim 12, further comprising determining a lateral position of the particle from an intensity pattern of the detected light.

18. The method according to claim 12, further comprising generating a signal proportional to the intensity of the light from a particle disposed at or near the sample region, and wherein the determining an axial position of the particle comprises solving a function of a frequency of the signal.

19. The method according to claim 12, wherein determining an axial position of the particle from an intensity pattern of the detected light includes calculating a Fourier transform of the intensity pattern of the detected light.

20. The method of claim 12, wherein determining the axial position of the particle from the intensity pattern of the detected light comprises:

receiving a time series signal from the light detector;

windowing the time series signal;

applying a Fast Fourier Transform (FFT) to the time series signal to produce a spectral density signal;

applying an inverse FFT (IFFT) to the spectral density signal to produce a temporal domain signal;

applying one or more signal processing steps to the temporal domain signal;

digitally propagating the processed temporal domain signal into a two dimensional signal;

applying a FFT to the two dimensional signal with respect to a lateral spatial frequency domain to produce a numerically reconstructed image in a two-dimensional image space; and determining the axial position of the particle from the numerically reconstructed image.

* * * * *